(12) United States Patent
Linemann et al.

(10) Patent No.: US 7,557,203 B2
(45) Date of Patent: Jul. 7, 2009

(54) EXPRESSION CASSETTES FOR THE BI-DIRECTIONAL TRANSGENIC EXPRESSION OF NUCLEIC ACIDS IN PLANTS

(75) Inventors: Ute Linemann, Gatersleben (DE); Karin Herbers, Neustadt (DE); Irene Kunze, Gatersleben (DE)

(73) Assignee: SunGene GmbH, Gatersleben (DE)

( * ) Notice: Subject to any disclaimer, the term of this patent is extended or adjusted under 35 U.S.C. 154(b) by 124 days.

(21) Appl. No.: 10/565,221

(22) PCT Filed: Jul. 3, 2004

(86) PCT No.: PCT/EP2004/007255

§ 371 (c)(1),
(2), (4) Date: Feb. 28, 2006

(87) PCT Pub. No.: WO2005/019459

PCT Pub. Date: Mar. 3, 2005

(65) Prior Publication Data

US 2006/0150282 A1 Jul. 6, 2006

(30) Foreign Application Priority Data

Jul. 22, 2003 (DE) ................. 103 33 479

(51) Int. Cl.
| | |
|---|---|
| C12N 15/82 | (2006.01) |
| C12N 15/00 | (2006.01) |
| A01H 5/00 | (2006.01) |
| A01H 5/10 | (2006.01) |
| C12N 15/11 | (2006.01) |
| C12N 15/63 | (2006.01) |

(52) U.S. Cl. .................. 536/24.1; 536/23.1; 435/320.1; 435/468; 800/278; 800/285; 800/295; 800/298

(58) Field of Classification Search ........................ None
See application file for complete search history.

(56) References Cited

U.S. PATENT DOCUMENTS

2002/0108142 A1 8/2002 Kapranov et al.

FOREIGN PATENT DOCUMENTS

| CA | 2 454 127 | 1/2003 |
| WO | WO-01/98480 | 12/2001 |
| WO | WO0198480 A2 * | 12/2001 |
| WO | WO-02/064804 | 8/2002 |

OTHER PUBLICATIONS

Benfey et al Science 250: 959-966.*
Sequence 315 from Patent WO0198480, *Arabidopsis thaliana* (thale cress), EMBL Accession No. AX461386, Jul. 8, 2002.
*Arabidopsis thaliana* oasA1 Gene for O-acetylserine (thiol) Lyase A1, exons 1-11, EMBL Accession No. AJ272027, Feb. 9, 2000.
Kausch, A. P. et al., "Characterization and Functional Analysis of a Bidirectional Promoter from Arabidopsis", Plant Biology, 2001, vol. 2001, p. 151.
"Lotus japonicus Phosphatidylinositol Transfer-Like Protein IV (LjPLP-IV) Gene, Complete cds;", GenBank Accession No. AF367434, Jun. 19, 2001.
"*Arabidopsis thaliana* DNA Chromosome 4, ESSA I FAC Contig Fragment No. 2", GenBank Accession No. Z97337, Jul. 4, 1997.
Jost, R. et al., "Genomic and Functional Characterization of the *oas* Gene Family Encoding O-acetylserine (thiol) Lysases, Enzymes Catalyzing the Final Step in Cysteine Biosynthesis in *Arabidopsis thaliana*", Gene, 2000, vol. 253, pp. 237-247.
Xie, M. et al., "Bidirectionalization of Polar Promoters in Plants", Nature Biotechnology, 2001, vol. 19, pp. 677-679.
Dong, J. Z. et al., "Transformation of Melon (*Cucumis melo* L.) and Expression from the Cauliflower Mosaic Virus 35S Promoter in Transgenic Melon Plants", Bio/Technology, 1991, vol. 9, pp. 858-863.

* cited by examiner

*Primary Examiner*—Russell Kallis
*Assistant Examiner*—Brent Page
(74) *Attorney, Agent, or Firm*—Connolly Bove Lodge & Hutz LLP

(57) ABSTRACT

The invention relates to transgenic expression cassettes for expressing two nucleic acid sequences in a plant cell comprising at least one regulatory sequence selected from the group consisting of
a) the promoter shown in SEQ ID NO: 1 or 2,
b) functional equivalents of the promoter shown in SEQ ID NO: 1 or 2 which have an identity of at least 80% to the sequence shown in SEQ ID NO: 1 or 2 and which have substantially the same promoter activity as the promoter shown in SEQ ID NO: 1 or 2,
c) functional equivalents of the promoter shown in SEQ ID NO: 1 or 2 which comprise at least 25 consecutive nucleotides of the sequences shown in SEQ ID NO: 1 or 2 and which have substantially the same promoter activity as the promoter shown in SEQ ID NO: 1 or 2, and
d) functionally equivalent fragments of sequences a) or b) or c), which have at least 25 consecutive nucleotides of said sequences a) or b) or c) and have substantially the same promoter activity as the promoter shown in SEQ ID NO: 1 or 2,
where said regulatory element is disposed between two nucleic acid sequences and is heterogeneous in relation to said nucleic acid sequences and is functionally linked to said nucleic acid sequences in such a way that the expression of two different ribonucleic acid sequences is brought about in at least one plant cell, where said ribonucleic acid sequences are selected from ribonucleic acid sequences coding for
i) amino acid sequences or
ii) ribonucleic acid sequences which bring about a reduction in the expression of at least one endogenous gene of said plant cell.

28 Claims, 2 Drawing Sheets

EXPRESSION CASSETTES FOR THE BI-DIRECTIONAL TRANSGENIC EXPRESSION OF NUCLEIC ACIDS IN PLANTS

RELATED APPLICATIONS

This application is a national stage application (under 35 U.S.C. 371) of PCT/EP2004/007255 filed Jul. 3, 2004 which claims benefit to German application 103 33 479.3 filed Jul. 22, 2003.

The invention relates to expression cassettes and vectors which comprise plant bidirectional promoters, and to the use of these expression cassettes or vectors for transgenic expression of nucleic acid sequences in plant organisms. The invention further relates to transgenic plant organisms transformed with these expression cassettes or vectors, to cultures, parts or propagation material derived therefrom, and to the use of the same for producing human and animal foods, seeds, pharmaceuticals or fine chemicals.

The production of transgenic plants is a fundamental technique of plant biotechnology and thus an indispensible prerequisite for fundamental research on plants, and for producing plants having improved, novel properties for agriculture, for increasing the quality of human foods or for producing particular chemicals or pharmaceuticals. A basic prerequisite for transgenic expression of particular genes in plants is the provision of plant-specific promoters. Various plant promoters are known. The constitutive promoters which are currently predominantly used in plants are almost exclusively viral promoters or promoters isolated from *Agrobacterium* such as, for example, the cauliflower mosaic virus promoter CaMV355 (Odell et al. (1985) Nature 313:810-812). The increasing complexity of the work in plant biotechnology often requires transformation with a plurality of expression constructs. Multiple use of one and the same promoter is problematic especially in plants, because the multiple presence of identical regulatory sequences may result in gene activity being switched off (silencing) (Kumpatla et al. (1998) TIBS 3:97-104; Selker (1999) Cell 97:157-160). There is thus an increasing need for novel promoters. An alternative way of dealing with this problem is the use of so-called "bidirectional" promoters, i.e. regulatory sequences which result in transcription of the upstream and downstream DNA sequences in both direction. It is possible in this case for example for target gene and marker gene to be introduced into a cell under the control of one DNA sequence.

Transgenic expression under the control of bidirectional promoters has scarcely been described to date. The production of bidirectional promoters from polar promoters for expression of nucleic acids in plants by means of fusion with further transcriptional elements has been described (Xie M (2001) Nature Biotech 19: 677-679). The 35S promoter has likewise been converted into a bidirectional promoter (Dong J Z et al. (1991) BIO/TECHNOLOGY 9: 858-863). WO 02/64804 describes the construction of a bidirectional promoter complex based on fusion of enhancer and nuclear promoter elements of various viral (CaMV 35S, CsVMV) and plant (Act2, PRb1b) sequences. US20020108142 describes a regulatory sequence from an intron of the phosphatidylinositol transfer-like protein IV from *Lotus japonicus* (PLP-IV; GenBank Acc. No.: AF367434) and the use thereof as bidirectional promoter. This intron fragment has a transcriptional activity only in the infection zone of the nodules. Other tissues, roots, leaves or flowers show no stain.

Plant promoters permitting bidirectional, ubiquitous (i.e. substantially tissue-nonspecific) and constitutive expression in plants have not been disclosed to date.

WO 03/006660 describes a promoter of a putative ferredoxin gene, and expression constructs, vectors and transgenic plants comprising this promoter. The isolated 836 bp 5'-flanking sequence fused to the glucuronidase gene surprisingly show a constitutive expression pattern in transgenic tobacco. The sequence corresponds to a sequence segment on chromosome 4 of *Arabidopsis thaliana* as deposited in GenBank under the Acc. No. Z97337 (version Z97337.2; base pair 85117 to 85952; the gene starting at bp 85953 is annotated with strong similarity to ferredoxin [2Fe-2S] I, Nostoc muscorum"). The activity detectable in the anthers/pollen of the closed flower buds was only weak, and in mature flowers was zero. Contrary to the prejudice derived from the literature findings against suitability of the promoter for efficient expression of selection markers (for example based on the presumed leaf specificity or the function in photosynthetic electron transport), it was possible to demonstrate highly efficient selection by combination with, for example, the kanamycin resistant gene (nptII). WO 03/006660 describes merely the use as "normal" constitutive promoter. Use as bidirectional promoter is not disclosed.

In order to integrate a maximum number of genes into a plant genome via a transfer complex, it is necessary to limit the number and size of regulatory sequences for expressing transgenic nucleic acids. Promoters acting bidirectionally contribute to achieving this object. It is particularly advantageous to use a bidirectional promoter when its activities are present coordinated in the same strength and are located on a short DNA fragment. Since there is little acceptance for the use of viral sequences for expression in transgenic plants, it is advantageous to use regulatory sequences which are likewise from plants.

The object on which the present invention was based was to provide transgenic expression cassettes comprising plant regulatory sequences which mediate bidirectional, ubiquitous and development-independent (constitutive) expression of two nucleic acid sequences which are to be expressed transgenically.

This object is achieved by the present invention. The first aspect of the invention therefore relates to expression cassettes for transgenic expression of two nucleic acid sequences in a plant cell comprising at least one regulatory sequence selected from the group consisting of a) the promoter shown in SEQ ID NO: 1 or 2,
b) functional equivalents of the promoter shown in SEQ ID NO: 1 or 2 which have an identity of at least 80% to the sequence shown in SEQ ID NO: 1 or 2 and which have substantially the same promoter activity as the promoter shown in SEQ ID NO: 1 or 2,
b) functional equivalents of the promoter shown in SEQ ID NO: 1 or 2 which comprise at least 25 consecutive nucleotides of the sequences shown in SEQ ID NO: 1 or 2 and which have substantially the same promoter activity as the promoter shown in SEQ ID NO: 1 or 2, and
c) functionally equivalent fragments of sequences a) or b) or c), which have at least 25 consecutive nucleotides of said sequences a) or b) or c) and have substantially the same promoter activity as the promoter shown in SEQ ID NO: 1 or 2, where said regulatory element is disposed between two nucleic acid sequences and is heterogeneous in relation to said nucleic acid sequence and is functionally linked to said nucleic acid sequences in such a way that the expression of two different ribonucleic acid sequences is brought about in at least one plant cell, where said ribonucleic acid sequences are selected from ribonucleic acid sequences coding for
i) amino acid sequences or
ii) ribonucleic acid sequences which bring about a reduction in the expression of at least one endogenous gene of said plant cell.

The invention further relates to a process for transgenic expression of two ribonucleic acid sequences in plant cells, where an expression cassettes comprising at least one regulatory sequence selected from the group consisting of
a) the promoter shown in SEQ ID NO: 1 or 2,
b) functional equivalents of the promoter shown in SEQ ID NO: 1 or 2 which have an identity of at least 80% to the sequence shown in SEQ ID NO: 1 or 2 and which have substantially the same promoter activity as the promoter shown in SEQ ID NO: 1 or 2,
b) functional equivalents of the promoter shown in SEQ ID NO: 1 or 2 which comprise at least 25 consecutive nucleotides of the sequences shown in SEQ ID NO: 1 or 2 and which have substantially the same promoter activity as the promoter shown in SEQ ID NO: 1 or 2, and
c) functionally equivalent fragments of sequences a) or b) or c), which have at least 25 consecutive nucleotides of said sequences a) or b) or c) and have substantially the same promoter activity as the promoter shown in SEQ ID NO: 1 or 2, is introduced into at least one plant cell, where said regulatory element is disposed between two nucleic acid sequences and is heterogeneous in relation to said nucleic acid sequence and is functionally linked to said nucleic acid sequences in such a way that the expression of said two different ribonucleic acid sequences is brought about in at least said plant cell, where said ribonucleic acid sequences are selected from ribonucleic acid sequences coding for
i) amino acid sequences or
ii) ribonucleic acid sequences which bring about a reduction in the expression of at least one endogenous gene of said plant cell.

The DNA sequence employed in the present invention as bidirectional promoter corresponds to the intergene region between a putative ferredoxin (FD) gene and a putative O-acetylserine lyase (OASTL) gene in *Arabidopsis thaliana*.

It has been possible to achieve particularly good results in plants of the Brassicaceae family such as, for example, *arabidopsis* or oilseed rape. However, it was also possible to achieve very good results (especially on expression of selection markers) in other plant species (such as, for example, tobacco). The expression "activity" is substantially independent of the nature of the downstream nucleic acid. The use of the bidirectional promoter is suitable both for the expression of selection markers and for any other nucleic acid.

In a preferred embodiment, therefore, the two nucleic acid sequences to be expressed transgenically and comprised in the expression cassettes of the invention, or the ribonucleic acid sequences expressed in the process of the invention, are different. "Different" means in this connection that the ribonucleic acid sequences which are expressed transgenically starting from both sides of the bidirectional promoter differ from one another in at least one base. The two nucleic acid sequences preferably code for different proteins, preferably for proteins differing in function and/or activity.

The invention makes it possible to increase the number of transcription units with a reduced number of promoter sequences. In the case of translation fusions it is also possible to regulate more than two proteins. A particular advantage of this invention is that the expression of these multiple transgenes takes place simultaneously and synchronously under the control of the bidirectional promoter. The promoter is particularly suitable for coordinating expression of nucleic acids. Thus, it is possible to express simultaneously
i) target protein and selection marker or reporter protein
ii) selection marker and reporter protein
ii) two target proteins, e.g. from the same metabolic pathway
iii) sense and antisense RNA
iv) various proteins for defense against pathogens and many more, and bring about improved effects in the plants.

"Expression" comprises the transcription of the nucleic acid sequence which is to be expressed transgenically, but may also—in the case of an open reading frame in the sense orientation—include translation of the transcribed RNA of the nucleic acid sequence which is to be expressed transgenically into a corresponding polypeptide.

"Expression cassette for transgenic expression of nucleic acids or process for transgenic expresssion of nucleic acids comprises all those constructions or processes brought about by genetic engineering methods, in which either
a) one of the promoters of the invention (e.g. the promoter shown in SEQ ID NO: 1 or 2 or a functional equivalent thereof), or
b) the nucleic acid sequence which is to be expressed under the control of said promoter, or
c) (a) and (b)

are not in their natural genetic environment (i.e. at their natural chromosomal locus) or have been modified by genetic engineering methods, it being possible for the modification to be for example a substitution, addition, deletion, inversion or insertion of one or more nucleotide residues. In a preferred embodiment, the nucleic acid sequence which is to be expressed under the control of one of the promoters of the invention is heterologous in relation to said promoter, i.e. it is not naturally under the control thereof, but said control has been produced in a non-natural manner (for example by genetic engineering processes).

The expression cassettes of the invention, vectors derived therefrom or the processes of the invention may comprise functional equivalents to the promoter sequences described in SEQ ID NO: 1 or 2. Functionally equivalent sequences also comprise all the sequences derived from the complementary counterpart strand of the sequences defined by SEQ ID NO: 1 or 2, and have substantially the same promoter activity. Functional equivalents in relation to the promoters of the invention means in particular natural or artificial mutations of the promoter sequences described in SEQ ID NO: 1 or 2, and their homologs from other plant genera and species which still have substantially the same promoter activity.

A promoter activity is referred to as substantially the same if the transcription of a particular gene to be expressed under the control of a particular promoter derived from SEQ ID NO: 1 or 2 under conditions which are otherwise unchanged exhibits a localization within the plant which is at least 50%, preferably at least 70%, particularly preferably at least 90%, very particularly preferably at least 95% coincident with a comparative expression obtained using one of the promoter described by SEQ ID NO: 1 or 2. It is possible in this case for the level of expression to differ both downward and upward from a comparison value. Sequences preferred in this connection are those whose level of expression, measured by means of the transcribed mRNA or the subsequently translated protein, under conditions which are otherwise unchanged, differs quantitatively by not more than 50%, preferably 25%, particularly preferably 10% from a comparison value obtained with a promoter described by SEQ ID NO: 1 or 2. Particularly preferred sequences are those whose level of expression, measured by means of the transcribed mRNA or the subsequently translated protein, under conditions which are otherwise unchanged, exceeds quantitatively by more than 50%, preferably 100%, particularly preferably 500%, very particularly preferably 1000% a comparison value obtained with the promoter described by SEQ ID NO:1. The preferred comparison value is the level of expression of the natural mRNA of the particular gene or of the natural gene product. A further preferred comparison value is the level of expression obtained with any defined nucleic acid sequence, preferably those nucleic acid sequences which code for easily quantifiable proteins. Very particular preference is given in this connection to reporter proteins (Schenborn E & Groskreutz D (1999) Mol Biotechnol 13(1):29-44) such as the "green fluorescence protein" (GFP) (Chui W L et al., Curr Biol 1996, 6:325-330; Leffel S M et al., Biotechniques. 23(5): 912-8, 1997), chloramphenicol transferase, a luciferase (Millar et al., Plant Mol Biol Rep 1992 10:324-414) or β-galactosidase, with very particular preference for β-glucuronidase (Jefferson et al. (1987) EMBO J. 6:3901-3907).

Conditions which are otherwise unchanged means that the expression initiated by one of the expression cassettes to be compared is not modified by combination with additional genetic control sequences, for example enhancer sequences. Unchanged conditions means that all general conditions such as, for example, plant species, stage of plant development, culturing conditions, assay conditions (such as buffer, temperature, substrates etc.) are kept identical between the expressions to be compared.

Mutations comprise substitutions, additions, deletions, inversions or insertions of one or more nucleotide residues. Thus, the present invention also comprises for example nucleic acid sequences which are obtained by modification of a promoter as shown in SEQ ID NO: 1 or 2. The aim of a modification of this type may be further delimitation of the sequence contained therein or, for example, else insertion of further restriction enzyme cleavage sites, deletion of redundant DNA or addition of further sequences, for example further regulatory sequences.

Where insertions, deletions of substitutions such as, for example, transitions and transversions are appropriate, it is possible to use techniques known per se, such as in vitro mutagenesis, primer repair, restriction or ligation. Complementary ends of the fragments can be made available for ligation by manipulations such as, for example, restriction, chewing-back or filling in of protrusions for blunt ends. Analogous results can also be obtained by using the polymerase chain reaction (PCR) using specific oligonucleotide primers.

Identity between two nucleic acids means the identity of the nucleic acid sequence over the entire sequence length in each case, which is calculated by comparison with the aid of the GAP program algorithm (Wisconsin Package Version 10.0, University of Wisconsin, Genetics Computer Group (GCG), Madison, USA), setting the following parameters:

| Gap Weight: 12 | Length Weight: 4 |
|---|---|
| Average Match: 2,912 | Average Mismatch: −2,003 |

For example, a sequence which has an identity of at least 50% based on nucleic acids with the sequence of SEQ ID NO: 1 means a sequence which has an identity of at least 50% on comparison with the sequence SEQ ID NO: 1 by the above program algorithm with the above set of parameters.

Functional equivalents to the promoter shown in SEQ ID NO: 1 preferably comprises those sequences which have an identity of at least 80%, preferably 90%, particularly preferably at least 95%, very particularly preferably at least 98%, most preferably 99%, to the sequence shown in SEQ ID NO: 1 and additionally exhibits substantially the same promoter activity as the sequence shown in SEQ ID NO: 1.

Functional equivalents to the promoter shown in SEQ ID NO: 2 preferably comprises those sequences which have an identity of at least 80%, preferably 90%, particularly preferably at least 95%, very particularly preferably at least 98%, most preferably 99%, to the sequence shown in SEQ ID NO: 2 and additionally exhibits substantially the same promoter activity as the sequence shown in SEQ ID NO: 2.

Further examples of the promoter sequences employed in the expression cassettes or vectors of the invention can be easily found for example in various organisms whose genomic sequence is known, such as, for example, from *Arabidopsis thaliana, Brassica napus, Nicotiana tabacum, Solanum tuberosum, Helianthium annuus, Linum sativum* by identity comparisons in data bases.

Process for producing functional equivalents of the invention preferably comprises the introduction of mutations into a promoter shown in SEQ ID NO: 1. A mutagenesis may take place randomly, in which case the mutagenized sequences are subsequently screened for their properties by a trial-by-error procedure. Particularly advantageous selection criteria comprise for example an increased resistance to a selection marker, the level of the resulting expression of the introduced nucleic acid sequence.

In a further embodiment of the invention it is possible for essential regulatory elements of the promoters of the invention to be isolated in a targeted manner and employed as such or in combination with other regulatory elements. Consequently, one aspect of the invention comprises functional equivalents of the promoter shown in SEQ ID NO: 1 or 2 which comprise at least 25, preferably at least 50, particularly preferably at least 100, very particularly preferably at least 200, most preferably at least 400 consecutive nucleotides of the sequences shown in SEQ ID NO: 1 or 2 and have substantially the same promoter activity as the promoter shown in SEQ ID NO: 1 or 2.

Alternatively, nonessential sequences of one of the promoters of the invention can be deleted without significantly impairing the properties mentioned. A further aspect of the invention therefore comprises functionally equivalent fragments of one of the promoter sequences of the invention which have at least 25, preferably at least 50, particularly preferably at least 100, very particularly preferably at least 200, most preferably at least 400 consecutive nucleotides of one of the promoter sequences of the invention and have substantially the same promoter activity as the promoter shown in SEQ ID NO: 1 or 2.

Delimitation of the promoter sequence to particular essential regulatory regions can also be undertaken with the aid of a search routine to search for promoter elements. Frequently, particular promoter elements are present in large numbers in the regions relevant for the promoter activity. This analysis can be undertaken for example using computer programs such as the PLACE program ("Plant Cis-acting Regulatory DNA Elements") (Higo K et al. (1999) Nucleic Acids Res 27:1, 297-300) or the BIOBASE database "Transfac" (Biologische Datenbanken GmbH, Braunschweig).

Processes for mutagenizing nucleic acid sequences are known to the skilled worker and include by way of example the use of oligonucleotides having one or more mutations compared with the region to be mutated (e.g. within the framework of a site-specific mutagenesis). Primers having approximately 15 to approximately 75 nucleotides or more are typically employed, with preferably about 10 to about 25 or more nucleotide residues being located on both sides of the sequence to be modified. Details and procedure for said mutagenesis processes are familiar to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be achieved by treatment of, for example, vectors comprising one of the nucleic acid sequences of the invention with mutagenizing agents such as hydroxylamine.

The nucleic acid sequences which are present in the expression cassettes of the invention and are to be expressed transgenically may be functionally linked to further genetic control sequences besides one of the promoters of the invention.

A functional linkage means for example sequential arrangement of a promoter, of the nucleic acid sequence to be expressed transgenically and, if appropriate, further regulatory elements such as, for example, a terminator in such a way that each of the regulatory elements is able to fulfill its function in the transgenic expression of the nucleic acid sequence, depending on the arrangement of the nucleic acid sequences to give sense or antisense RNA. A direct linkage in the chemical sense is not absolutely necessary for this. Genetic control sequences such as, for example, enhancer sequences are also able to exert their function from remote positions or even from other DNA molecules on the target sequence. Preferred arrangements are those in which the nucleic acid sequence to be expressed transgenically is positioned behind the sequence acting as promoter, so that the two sequences are covalently connected together. In this connection, the distance between the promoter sequence and the nucleic acid sequence to be expressed transgenically is preferably less than 200 base pairs, particularly preferably less than 100 base pairs, very particularly preferably less than 50 base pairs.

Production of a functional linkage can be achieved by using conventional recombination and cloning techniques as described for example in Maniatis T et al. (1989) Molecular Cloning: A Laboratory Manual, Cold Spring Harbor Laboratory, Cold Spring Harbor, N.Y. and in Silhavy T J et al. (1984) Experiments with Gene Fusions, Cold Spring Harbor Laboratory, Cold Spring Harbor, N.Y. and in Ausubel F M et al. (1987) Current Protocols in Molecular Biology, Greene Publishing Assoc. and Wiley Interscience. However, further sequences which have for example the function of a linker with particular restriction enzyme cleavage sites or of a single peptide may also be positioned between the two sequences. Insertion of sequences may also lead to expression of fusion proteins.

The term genetic control sequences is to be understood broadly and means all sequences having an influence on the coming into existence of the function of the transgenic expression cassette of the invention. Genetic control sequences modify for example the transcription and translation in prokaryotic or eukaryotic organisms. The expression cassettes of the invention preferably comprise as additional genetic control sequence one of the promoters of the invention 5'-upstream from the particular nucleic acid sequence to be expressed transgenically, and a terminator sequence 3'-downstream, and if appropriate further usual regulatory elements, in each case functionally linked to the nucleic acid sequence to be expressed transgenically.

Genetic control sequences also comprise further promoters, promoter elements or minimal promoters which are able to modify the expression-controlling properties. It is thus possible for example through genetic control sequences for tissue-specific expression to take place additionally in dependence on particular stress factors. Corresponding elements are described for example for water stress, abscisic acid (Lam E and Chua N H, (1991) J Biol Chem 266(26):17131-17135) and heat stress (Schöffl F et al. (1989) Mol Gen Genetics 217(2-3):246-53).

A further possibility is for further promoters which make expression possible in further plant tissues or in other organisms such as, for example, E. coli bacteria to be functionally linked to the nucleic acid sequence to be expressed. Suitable plant promoters are in principle all the promoters described above. It is conceivable for example that a particular nucleic acid sequence is described by a promoter (for example one of the promoters of the invention) in one plant tissue as sense RNA and translated into the corresponding protein, while the same nucleic acid sequence is transcribed by another promoter with a different specificity in a different tissue into antisense RNA, and the corresponding protein is downregulated. This can be implemented by an expression cassette of the invention by the one promoter being positioned in front of the nucleic acid sequence to be expressed transgenically, and the other promoter behind.

Genetic control sequences further comprise also the 5'-untranslated region, introns or the noncoding 3' region of genes, preferably of the pFD gene and/or of the OASTL gene. It has been shown that untranslated regions may play a significant functions in the regulation of gene expression. Thus, it has been shown that 5'-untranslated sequences may enhance the transient expression of heterologous genes. They may moreover promote tissue specificity (Rouster J et al. (1998) Plant J. 15:435-440.). Conversely, the 5'-untranslated region of the opaque-2 gene suppresses expression. Deletion of the corresponding region leads to an increase in gene activity (Lohmer S et al. (1993) Plant Cell 5:65-73). The nucleic acid sequence indicated under SEQ ID NO: 2 comprises the segment of the FD gene and of the OASTL gene which represents the promoter and the 5'-untranslated region up to the ATG start codon of the respective protein. An intron is present in the 5' untranslated region of the OASTL gene, as can be proved by the structure of the cDNA clones. The intron limits are located at 14 bp (3' side of the intron) and 281 bp (5' side of the intron). Base pair numbering corresponding to the numbering of the promoter shown in SEQ ID NO: 2. The intron has a strong expression-promoting function in both directions of transcription. The reason for this might be the existence of an enhancer in this region.

In a preferred embodiment, therefore, the bidirectional promoter of the invention is described by the sequence shown in SEQ ID NO: 2 or by sequences which have an identity of at least 80%, preferably at least 90%, particularly preferably at least 95%, very particularly preferably at least 98%, most preferably at least 99% to the sequence shown in SEQ ID NO: 2.

Further 5'-untranslated sequences and introns with expression-promoting function are known to the skilled worker. McElroy and coworkers (McElroy et al. (1991) Mol Gen Genet 231(1):150-160) reported on a construct based on the rice actin 1 (Act1) promoter for transforming monocotyledonous plants. Use of the Act1 intron in combination with the 35S promoter in transgenic rice cells led to an expression rate which was increased ten-fold compared with the isolated 35S promoter. Optimization of the sequence environment of the translation initiation site of the reporter gene gene (GUS) resulted in a four-fold increase in GUS expression in transformed rice cells. Combination of the optimized translation initiation site and of the Act1 intron resulted in a 40-fold increase in GUS expression by the CaMV35S promoter in transformed rice cells; similar results have been obtained with transformed corn cells. Overall, it was concluded from the investigations described above that the expression vectors based on the Act1 promoter are suitable for controlling sufficiently strong and constitutive expression of foreign DNA in transformed cells of monocotyledonous plants.

The expression cassette may comprise one or more so-called enhancer sequences functionally linked to the promoter, which make increased transgenic expression of the nucleic acid sequence possible. It is also possible to insert additional advantageous sequences, such as further regulatory elements or terminators, at the 3' end of the nucleic acid sequences which are to be expressed transgenically. The nucleic acid sequences which are to be expressed transgenically may be present in one or more copies in one of the expression cassettes of the invention.

Control sequences additionally mean those which make homologous recombination or insertion into the genome of a host organism possible or which allow deletion from the genome. It is possible in homologous recombination for example for the natural promoter of a particular gene to be replaced by one of the promoters of the invention. Methods such as the creaox technology permit tissue-specific deletion, which is inducible in some circumstances, of the expression cassette from the genome of the host organism (Sauer B. (1998) Methods. 14(4):381-92). In this case, particular flanking sequences are attached (lox sequences) to the target gene and subsequently make deletion possible by means of cre recombinase.

The promoter to be introduced can be placed by means of homologous recombination in front of the target gene which is to be expressed transgenically by linking the promoter to DNA sequences which are, for example, homologous to endogenous sequences which precede the reading frame of the target gene. Such sequences are to be regarded as genetic control sequences. After a cell has been transformed with the appropriate DNA construct, the two homologous sequences can interact and thus place the promoter sequence at the desired site in front of the target gene, so that the promoter sequence is now functionally linked to the target gene and forms an expression cassette of the invention. The selection of the homologous sequences determines the promoter insertion site. It is possible in this case for the expression cassette to be generated by homologous recombination by means of single or double reciprocal recombination. In single reciprocal recombination there is use of only a single recombination sequence, and the complete introduced DNA is inserted. In double reciprocal recombination the DNA to be introduced is flanked by two homologous sequences, and the flanking region is inserted. The latter process is suitable for replacing, as described above, the natural promoter of a particular gene by one of the promoters of the invention and thus modifying the location and timing of gene expression. This functional linkage represents an expression cassette of the invention.

To select successfully homologously recombined or else transformed cells it is usually necessary additionally to introduce a selectable marker. Various suitable markers are mentioned below. The selection marker permits selection of transformed from untransformed cells. Homologous recombination is a relatively rare event in higher eukaryotes, especially in plants. Random integrations into the host genome predominate. One possibility of deleting randomly integrated sequences and thus enriching cell clones having a correct homologous recombination consists of using a sequence-specific recombination system as described in U.S. Pat. No. 6,110,736.

Polyadenylation signals suitable as control sequences are plant polyadenylation signals and—preferably—those from *Agrobacterium tumefaciens*. In a particularly preferred embodiment, the expression cassette comprises a terminator sequence which is functional in plants. Terminator sequences which are functional in plants means in general sequences able to bring about termination of transcription of a DNA sequence in plants. Examples of suitable terminator sequences are the OCS (octopine synthase) terminator and the NOS (nopaline synthase) terminator. However, plant terminator sequences are particularly preferred. Plant terminator sequences means in general sequences which are a constituent of a natural plant gene. Particular preference is given in this connection to the terminator of the potato cathepsin D inhibitor gene (GenBank Acc. No.: X74985) or of the terminator of the field bean storage protein gene VfLEIB3 (GenBank Acc. No.: Z26489). These terminators are at least equivalent to the viral or T-DNA terminators described in the art.

The skilled worker is aware of a large number of nucleic acids and proteins whose recombinant expression is advantageous under the control of the expression cassettes or processes of the invention. The skilled worker is further aware of a large number of genes through whose repression or switching off by means of expression of an appropriate antisense RNA it is possible likewise to achieve advantageous effects. Non-restrictive examples of advantageous effects which may be mentioned are:

facilitated production of a transgenic organism for example through the expression of selection markers achievement of resistance to abiotic stress factors (heat, cold, aridity, increased moisture, environmental toxins, UV radiation)

achievement of resistance to biotic stress factors (pathogens, viruses, insects and diseases)

improvement in human or animal food properties improvement in the growth rate of the yield.

Some specific examples of nucleic acids whose expression provides the desired advantageous effects may be mentioned below:

1. Selection Markers

Selection marker comprises both positive selection markers which confer resistance to an antibiotic, herbicide or biocide, and negative selection markers which confer sensitivity to precisely the latter, and markers which provide the transformed organism with a growth advantage (for example through expression of key genes of cytokine biosynthesis; Ebinuma H et al. (2000) Proc Natl Acad Sci USA 94:2117-2121). In the case of positive selection, only the organisms which express the corresponding selection marker thrive, whereas in the case of negative selection it is precisely these which perish. The use of a positive selection marker is preferred in the production of transgenic plants. It is further preferred to use selection markers which confer growth advantages. Negative selection markers can be used advantageously if the intention is to delete particular genes or genome sections from an organism (for example as part of a cross-breeding process).

The selectable marker introduced with the expression cassette confers resistance to a biocide (for example a herbicide such as phosphinothricin, glyphosate or bromoxynil), a metabolism inhibitor such as 2-deoxyglucose 6-phosphate (WO 98/45456) or an antibiotic such as, for example, kanamycin, G 418, bleomycin, hygromycin, on the successfully recombined or transformed cells. The selection marker permits selection of transformed from transformed from untransformed cells (McCormick et al. (1986) Plant Cell Rep 5:81-84). Particularly preferred selection markers are those which confer resistance to herbicides. The skilled worker is aware of numerous selection markers of this type and the sequences coding therefor. Non-restrictive examples may be mentioned below:

i) Positive Selection Markers:

The selectable marker introduced with the expression cassette confers resistance to a biocide (for example a herbicide such as phosphinothricin, glyphosate or bromoxynil), a metabolism inhibitor such as 2-deoxyglucose 6-phosphate (WO 98/45456) or an antibiotic such as, for example, tetracycline, ampicillin, kanamycin, G 418, neomycin, bleomycin or hygromycin, on the successfully transformed cells. The selection marker permits selection of transformed from untransformed cells (McCormick et al. (1986) Plant Cell Rep 5:81-84). Particularly preferred selection markers are those which confer resistance to herbicides. Examples of selection markers which may be mentioned are:

DNA sequences which code for phosphinothricin acetyltransferases (PAT; also called bialophos resistance gene (bar)) and bring about detoxification of the herbicide phosphinothricin (PPT) (de Block et al. (1987) EMBO J 6:2513-2518). Suitable bar genes can be isolated from, for example, *Streptomyces hygroscopicus* or *S. viridochromogenes*. Corresponding sequences are known to the skilled worker (GenBank Acc. No.: X17220, X05822, M22827, X65195; U.S. Pat. No. 5,489,520). Also described are synthetic genes for example for expression in plastids AJ028212. A synthetic Pat gene is described in Becker et al. (1994) Plant J 5:299-307. The genes confer resistance to the herbicide bialaphos and are a widely used marker in transgenic plants (Vickers J E et al. (1996) Plant Mol Biol Rep 14:363-368; Thompson C J et al. (1987) EMBO J 6:2519-2523).

5-enolpyruvylshikimate-3-phosphate synthase genes (EPSP synthase genes) which confer resistance to glyphosate (N-(phosphonomethyl)glycine) (Steinrucken H C et al. (1980) Biochem Biophys Res Commun 94:1207-1212; Levin J G and Sprinson D B (1964) J Biol Chem 239:1142-1150; Cole D J (1985) Mode of action of glyphosate; A literature analysis, p. 48-74. In: Grossbard E and Atkinson D (eds.). The herbicide glyphosate. Buttersworths, Boston.). Glyphosate-tolerant EPSPS variants are preferably used as selection markers (Padgette S R et al. (1996). New weed control opportunities: development of soybeans with a Roundup Ready™ gene. In: Herbicide Resistant Crops (Duke S O ed.), pp. 53-84. CRC Press, Boca Raton, Fla.; Saroha M K und Malik V S (1998) J Plant Biochem Biotechnol 7:65-72). The EPSPS gene of the *Agrobacterium* sp. strain CP4 has a natural glyphosate tolerance which can be transferred to appropriate transgenic plants (Padgette S R et al. (1995) Crop Science 35(5):1451-1461). 5-Enolpyrvylshikimate-3-phosphate synthases which are glyphosate-tolerant are described for example in U.S. Pat. No. 5,510,471; U.S. Pat. No. 5,776,760; U.S. Pat. No. 5,864,425; U.S. Pat. No. 5,633,435; U.S. Pat. No. 5,627,061; U.S. Pat. No. 5,463,175; EP 0 218 571. Further sequences are described under GenBank Accession X63374. The aroA gene is further preferred (M10947).

the gox gene (glyphosate oxide reductase from *Achromobacter* sp.) coding for the glyphosate-degrading enzymes. GOX can confer resistance to glyphosate (Padgette S R et al. (1996) J Nutr. 126(3):702-16; Shah D et al. (1986) Science 233: 478-481).

the deh gene (coding for a dehalogenase which inactivates dalapon), (GenBank Acc. No.: AX022822, AX022820 and WO99/27116)

bxn genes which code for bromoxynil-degrading nitrilase enzymes. For example the nitrilase from *Klebsiella ozanenae*. Sequences are to be found in GenBank for example under the Acc. No: E01313 and J03196.

neomycin phosphotransferases confer resistance to antibiotics (aminoglycosides) such as neomycin, G418, hygromycin, paromomycin or kanamycin by reducing their inhibiting effect through a phosphorylation reaction. The nptII gene is particularly preferred. Sequences can be obtained from GenBank (AF080390 minitransposon mTn5-GNm; AF080389 minitransposon mTn5-Nm, complete sequence). In addition, the gene is already a component of numerous expression vectors and can be isolated therefrom by using processes familiar to the skilled worker (such as, for example, polymerase chain reaction) (AF234316 pCAMBIA-2301; AF234315 pCAMBIA-2300, AF234314 pCAMBIA-2201). The NPTII gene codes for an aminoglycoside 3'O-phosphotransferase from *E. coli*, Tn5 (GenBank Acc. No: U00004 Position 1401-2300; Beck et al. (1982) Gene 19 327-336).

the $DOG^R1$ gene. The $DOG^R1$ gene was isolated from the yeast *Saccharomyces cerevisiae* (EP 0 807 836). It codes for a 2-deoxyglucose-6-phosphate phosphatase which confers resistance to 2-DOG (Randez-Gil et al. 1995, Yeast 11, 1233-1240; Sanz et al. (1994) Yeast 10:1195-1202, sequence: GenBank Acc. No.: NC001140 chromosome VIII, *Saccharomyces cervisiae* position 194799-194056).

sulfonylurea- and imidazolinone-inactivating acetolactate synthases which confer resistance to imidazolinone/sulfonylurea herbicides. Suitable examples are the sequence deposited under GenBank Acc No.: X51514 for the *Arabidopsis thaliana* Csr 1.2 gene (EC 4.1.3.18) (Sathasivan K et al. (1990) Nucleic Acids Res. 18(8): 2188). Acetolactate synthases which confer resistance to imidazolinone herbicides are also described under GenBank Acc. No.: AB049823, AF094326, X07645, X07644, A19547, A19546, A19545, I05376, I05373, AL133315.

hygromycin phosphotransferases (X74325 *P. pseudomallei* gene for hygromycin phosphotransferase) which confer resistance to the antibiotic hygromycin. The gene is a constituent of numerous expression vectors and can be isolated therefrom by using processes familiar to the skilled worker (such as, for example, polymerase chain reaction) (AF294981 pINDEX4; AF234301 pCAMBIA-1380; AF234300 pCAMBIA-1304; AF234299 pCAMBIA-1303; AF234298 pCAMBIA-1302; AF354046 pCAMBIA-1305; AF354045 pCAMBIA-1305.1)

Resistance genes for a) chloramphenicol (chloramphenicol acetyltransferase), b) tetracycline, various resistance genes are described, e.g. X65876 *S. ordonez* genes class D teta and tetR for tetracycline resistance and repressor proteins X51366 *Bacillus cereus* plasmid pBC16 tetracycline resistance gene. In addition, the gene is already a constituent of numerous expression vectors and can be isolated therefrom by using processes familiar to the skilled worker (such as, for example, polymerase chain reaction)

c) streptomycin, various resistance genes are described, e.g. with the GenBank Acc. No.: AJ278607 *Corynebacterium acetoacidophilum* ant gene for streptomycin adenylyltransferase.

d) zeocin, the corresponding resistance gene is a constituent of numerous cloning vectors (e.g. L36849 cloning vector pZEO) and can be isolated therefrom by using processes familiar to the skilled worker (such as, for example, polymerase chain reaction).

e) ampicillin (β-lactamase gene; Datta N, Richmond M H. (1966) Biochem J. 98(1):204-9; Heffron F et al (1975) J. Bacteriol 122: 250-256; the Amp gene was first cloned to prepare the *E. coli* vector pBR322; Bolivar F et al. (1977) Gene 2:95-114). The sequence is a constituent of numerous cloning vectors and can be isolated therefrom by using processes familiar to the skilled worker (such as, for example, polymerase chain reaction).

Genes such as the isopentenyltransferase from *Agrobacterium tumefaciens* (strain:PO22) (Genbank Acc. No.: AB025109). The ipt gene is a key enzyme in cytokine biosynthesis. Overexpression thereof facilitates regeneration of plants (e.g. selection on cytokine-free medium). The process for utilizing the ipt gene is described (Ebinuma H et al. (2000) Proc Natl Acad Sci USA 94:2117-2121; Ebinuma H et al. (2000) Selection of Marker-free transgenic plants using the onco-genes (ipt, rol A, B, C) of *Agrobacterium* as selectable markers, In Molecular Biology of Woody Plants. Kluwer Academic Publishers).

Various further positive selection markers which confer a growth advantage on the transformed plants compared with untransformed ones, and processes for their use are described inter alia in EP-A 0 601 092. Examples which should be mentioned are β-glucuronidase (in conjunction with, for example, cytokinin glucuronide), mannose-6-phosphate isomerase (in conjunction with mannose), UDP-galactose 4-epimerase (in conjunction with, for example, galactose), with particular preference for mannose-6-phosphate isomerase in conjunction with mannose.

ii) Negative Selection Markers

Negative selection markers make it possible for example to select organisms with successfully deleted sequences which comprise the marker gene (Koprek T et al. (1999) Plant J 19(6):719-726). In the case of negative selection, for example a compound which otherwise has no disadvantageous effect for the plant is converted into a compound having a disadvantageous effect by the negative selection marker introduced into the plant. Also suitable are genes which per se have a disadvantageous effect, such as, for example, thymidine kinase (TK), diphtheria toxin A fragment (DT-A), the codA gene product coding for a cytosine deaminase (Gleave A P et al. (1999) Plant Mol Biol. 40(2):223-35; Perera R J et al. (1993) Plant Mol. Biol 23(4): 793-799; Stougaard J (1993) Plant J 3:755-761), the cytochrome P450 gene (Koprek et al. (1999) Plant J 16:719-726), genes coding for a haloalkane dehalogenase (Naested H (1999) Plant J 18:571-576), the iaaH gene (Sundaresan V et al. (1995) Genes & Development 9:1797-1810) or the tms2 gene (Fedoroff N V & Smith D L (1993) Plant J 3:273-289).

The concentrations used in each case for the selection of antibiotics, herbicides, biocides or toxins must be adapted to the particular test conditions or organisms. Examples which may be mentioned for plants are kanamycin (Km) 50 mgA, hygromycin B 40 mg/l, phosphinothricin (ppt) 6 mgA.

It is also possible to express functional analogs of said nucleic acids coding for selection markers. Functional analogs means in this connection all the sequences which have substantially the same function, i.e. are capable of selecting transformed organisms. It is moreover perfectly possible for the functional analog to differ in other features. It may for example have a higher or lower activity or else possess further functionalities.

2. Improved protection of the plant against abiotic stress factors such as aridity, heat, or cold for example through overexpression of antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), farnesyltransferases (WO 99/06580), Pei Z M et al., Science 1998, 282: 287-290), ferritin (Deak M et al., Nature Biotechnology 1999, 17:192-196), oxalate oxidase (WO 99/04013; Dunwell J M Biotechnology and Genetic Engineering Reviews 1998, 15:1-32), DREB1A factor (dehydration response element B 1A; Kasuga M et al., Nature Biotechnology 1999, 17:276-286), genes of mannitol or trehalose synthesis such as trehalose-phosphate synthase or trehalose-phosphate phosphatase (WO 97/42326), or by inhibition of genes such as of trehalase (WO 97/50561). Particularly preferred nucleic acids are those coding for the transcriptional activator CBF1 from *Arabidopsis thaliana* (GenBank Acc. No.: U77378) of the antifreeze protein from *Myoxocephalus octodecemspinosus* (GenBank Acc. No.: AF306348) or functional equivalents thereof.

3. Expression of metabolic enzymes for use in the animal and human food sectors, for example expression of phytase and cellulases. Particular preference is given to nucleic acids such as the artificial cDNA coding for a microbial phytase (GenBank Acc. No.: A19451) or functional equivalents thereof.

4. Achievement of resistance for example to fungi, insects, nematodes and diseases through targeted secretion or accumulation of particular metabolites or proteins in the epidermis of the embryo. Examples which may be mentioned are glucosinolates (defense against herbivors), chitinases or glucanases and other enzymes which destroy the cell wall of parasites, ribosome-inactivating proteins (RIPs) and other proteins of the plants' resistance and stress responses, as are induced on injury or microbial attack of plants or chemically by, for example, salicylic acid, jasmonic acid or ethylene, lysozymes from non-plant sources such as, for example, T4 lysozyme or lysozyme from various mammals, insecticidal proteins such as *Bacillus thuringiensis* endotoxin, α-amylase inhibitor or protease inhibitors (cowpea trypsin inhibitor), glucanases, lectins such as phytohemagglutinin, wheatgerm agglutinin, RNAses or ribozymes. Particularly preferred nucleic acids are those coding for the chit42 endochitinase from *Trichoderma harzianum* (GenBank Acc. No.: S78423) or for the N-hydroxylating, multifunctional cytochrome P-450 (CYP79) proteins from *Sorghum bicolor* (GenBank Acc. No.: U32624) or functional equivalents thereof.

5. The accumulation of glucosinolates in plants of the *Cardales* genus, especially the oil seeds to protect from pests (Rask L et al. (2000) Plant Mol Biol 42:93-113; Menard R et al. (1999) Phytochemistry 52:29-35), expression of the *Bacillus thuringiensis* endotoxin under the control of the 35S CaMV promoter (Vaeck et al. (1987) Nature 328:33-37) or protection of tobacco against fungal attack by expression of a bean chitonase under the control of the CaMV promoter (Broglie et al. (1991) Science 254:1194-119, is known.

The expression of synthetic cryIA(b) and cryIA(c) genes which code for the *lepidoptera*-specific delta endotoxins from *Bacillus thuringiensis* can bring about resistance to insect pests in various plants. Thus, it is possible in rice to achieve resistance to two of the principal rice pests, the striped stem borer (*Chilo suppressalis*) and the yellow stem borer (*Scirpophaga incertulas*) (Cheng X et al. (1998) Proc Natl Acad Sci USA 95(6):2767-2772; Nayak P et al. (1997) Proc Natl Acad Sci USA 94(6):2111-2116).

5. Expression of genes which bring about accumulation of fine chemicals such as of tocopherols, tocotrienols or carotenoids. An example which may be mentioned is phytoene desaturase. Nucleic acids which code for the phytoene desaturase from *Narcissus pseudonarcissus* (GenBank Acc. No.: X78815) or functional equivalents thereof are preferred.

6. Production of neutraceuticals such as, for example, polyunsaturated fatty acids such as, for example, arachidonic acid or EP (eicosapentaenoic acid) or DHA (docosahexaenoic acid) by expression of fatty acid elongases and/or desaturases or production of proteins having an improved nutritional value such as, for example, having a high content of essential amino acids (e.g. the methionine-rich 2S albumin gene of the Brazil nut). Preferred nucleic acids are those which code for the methionine-rich 2S albumin from *Bertholletia excelsa* (GenBank Acc. No.: AB044391), the Δ6-acyllipid desaturase from *Physcomitrella patens* (GenBank Acc. No.: AJ222980; Girke et al. (1998) Plant J 15:3948), the Δ6-desaturase from *Mortierelia alpina* (Sakuradani et al. (1999) Gene 238:445-453), the Δ5-desaturase from *Caenorhabditis elegans* (Michaelson et al. 1998, FEBS Letters 439:215-218), the Δ5-fatty acid desaturase (des-5) from *Caenorhabditis elegans* (GenBank Acc. No.: AF078796), the Δ5-desaturase from *Mortierella alpina* (Michaelson et al. J Biol Chem 273: 19055-19059), the Δ6-elongase from *Caenorhabditis elegans* (Beaudoin et al. (2000) Proc Natl. Acad Sci USA 97:6421-6426), the Δ6-elongase from *Physcomitrella patens* (Zank et al. (2000) Biochemical Society Transactions 28:654-657) or functional equivalents thereof.

7. Production of fine chemicals (such as, for example, enzymes) and pharmaceuticals (such as, for example, antibodies or vaccines as described in Hood E E, Jilka J M. (1999) Curr Opin Biotechnol. 10(4):382-6; Ma J K, Vine N D (1999) Curr Top Microbiol Immunol 236:275-92). It has been possible for example to produce recombinant avidin from chicken egg white and bacterial β-glucuronidase (GUS) on a large scale in transgenic corn plants (Hood et al. (1999) Adv Exp Med Biol 464:127-47). These recombinant proteins from corn plants are marketed as high-purity biochemicals by Sigma Chemicals Co.

8. Achieving an increased storage ability in cells which normally comprise few storage proteins or lipids with the aim of increasing the yield of these substances, for example by expression of an acetyl-CoA carboxylase. Preferred nucleic acids are those which code for the acetyl-CoA carboxylase (accase) from *Medicago sativa* (GenBank Acc. No.: L25042) or functional equivalents thereof.

Further examples of advantageous genes are mentioned for example in Dunwell J M (2000) J Exp Bot. 51 Spec No:487-96.

It is also possible to express functional analogs of said nucleic acids and proteins. Functional analogs means in this connection all the sequences which have substantially the same function, i.e. are capable of the function (for example a substrate conversion or signal transduction) like the protein mentioned by way of example too. It is moreover perfectly possible for the functional analog to differ in other features. It may for example have a higher or lower activity or else possess further functionalities. Functional analogs also means sequences which code for fusion proteins consisting of one of the preferred proteins and other proteins, for example a further preferred protein or else a signal peptide sequence.

Expression of the nucleic acids under the control of the promoters of the invention is possible in any desired cell compartment such as, for example, the endomembrane system, the vacuole and the chloroplasts. Desired glycosylation reactions, especially foldings and the like, are possible by utilizing the secretory pathway. Secretion of the target protein to the cell surface or secretion into the culture medium, for example on use of suspension-cultured cells or protoplasts, is also possible. The target sequences necessary for this purpose can thus be taken into account in individual vector variations and be introduced, together with the target gene to be cloned, into the vector through use of a suitable cloning strategy. It is possible to utilize as target sequences both gene-intrinsic, where present, or heterologous sequences. Additional heterologous sequences which are preferred for the functional linkage, but not restricted thereto, are further targeting sequences to ensure the subcellular localization in apoplasts, in the vacuole, in plastids, in the mitochondrion, in the endoplasmic reticulum (ER), in the cell nucleus, in elaioplasts or other compartments; and translation enhancers' such as the 5' leader sequence from tobacco mosaic virus (Gallie et al. (1987) Nucl Acids Res 15 8693-8711) and the like. The process for transporting proteins which are not localized per se in the plastids in a targeted fashion into the plastids is described (Klosgen R B & Weil J H (1991) Mol Gen Genet 225(2):297-304; Van Breusegem F et al. (1998) Plant Mol Biol 38(3):491-496). Preferred sequences are a) small subunit (SSU) of the ribulose-bisphosphate carboxylase (Rubisco ssu) from pea, corn, sunflower
b) transit peptides derived from genes of plant fatty acid biosynthesis such as the transit peptide of the plastidic acyl carrier protein (ACP), the stearyl-ACP desaturase, β-ketoacyl-ACP synthase or the acyl-ACP thioesterase
c) the transit peptide for GBSSI (starch granule bound starch synthase 1)
d) LHCP II genes.

The target sequences may be linked to other target sequences which differ from the transit peptide-encoding sequences in order to ensure a subcellular localization in the apoplast, in the vacuole, in plastids, in the mitochondrion, in the endoplasmic reticulum (ER), in the cell nucleus, in elaioplasts or other compartments. It is also possible to employ translation enhancers such as the 5' leader sequence from tobacco mosaic virus (Gallie et al. (1987) Nucl Acids Res 15:8693-8711) and the like.

The skilled worker is also aware that he need not express the genes described above directly by use of the nucleic acid sequences coding for these genes, or repress them for example by anti-sense. He can also use for example artificial transcription factors of the type of zinc finger proteins (Beerli R R et al. (2000) Proc Natl Acad Sci USA 97(4):1495-500). These factors bind in the regulatory regions of the endogenous genes which are to be expressed or repressed and result, depending on the design of the factor, in expression or repression of the endogenous gene. Thus, the desired effects can also be achieved by expression of an appropriate zinc finger transcription factor under the control of one of the promoters of the invention.

The expression cassettes of the invention can likewise be employed for suppressing or reducing replication or/and translation of target genes by gene silencing.

The expression cassettes of the invention can also be employed for expressing nucleic acids which mediate so-called antisense effects and are thus able for example to reduce the expression of a target protein.

Preferred genes and proteins whose suppression is the condition for an advantageous phenotype comprise by way of example, but non-restrictively:

a) polygalacturonase to prevent cell degradation and mushiness of plants and fruits, tomatoes for example. Preferably used for this purpose are nucleic acid sequences such as that of the tomato polygalacturonase gene (GenBank Acc. No.: X14074) or its homologs from other genera and species.

b) reduction in the expression of allergenic proteins as described for example in Tada Y et al. (1996) FEBS Lett 391(3):341-345 or Nakamura R (1996) Biosci Biotechnol Biochem 60(8):1215-1221.

c) changing the color of flowers by suppression of the expression of enzymes of anthocyan biosynthesis. Corresponding procedures are described (for example in Forkmann G, Martens S. (2001) Curr Opin Biotechnol 12(2):155-160). Preferably used for this purpose are nucleic acid sequences like that of flavonoid 3'-hydroxylase (GenBank Acc. No.: AB045593), of dihydroflavanol 4-reductase (GenBank Acc. No.: AF017451), of chalcone isomerase (GenBank Acc. No.: AF276302), of chalcone synthase (GenBank Acc. No.: AB061022), of flavanone 3-beta-hydroxylase (GenBank Acc. No.: X72592) or of flavone synthase II (GenBank Acc. No.: AB045592) or their homologs from other genera and species.

d) shifting the amylose/amylopectin content in starch by suppression of branching enzyme Q, which is responsible for $\alpha$-1,6-glycosidic linkage. Corresponding procedures are described (for example in Schwall G P et al. (2000) Nat Biotechnol 18(5):551-554). Preferably used for this purpose are nucleic acid sequences like that of the starch branching enzyme II of potato (GenBank Acc. No.: AR123356; U.S. Pat. No. 6,169,226) or its homologs from other genera and species.

An "antisense" nucleic acid means primarily a nucleic acid sequence which is wholly or partly complementary to at least part of the sense strand of said target protein. The skilled worker is aware that he can use alternatively the cDNA or the corresponding gene as starting template for corresponding antisense constructs. The antisense nucleic acid is preferably complementary to the coding region of the target protein or a part thereof. The antisense nucleic acid may, however, also be complementary to the non-coding region of a part thereof. Starting from the sequence information for a target protein, an antisense nucleic acid can be designed in a manner familiar to the skilled worker by taking account of the base-pair rules of Watson and Crick. An antisense nucleic acid may be complementary to the whole or a part of the nucleic acid sequence of a target protein. In a preferred embodiment, the antisense nucleic acid is an oligonucleotide with a length of for example 15, 20, 25, 30, 35, 40, 45 or 50 nucleotides.

The antisense nucleic acid comprises in a preferred embodiment $\alpha$-anomeric nucleic acid molecules. $\alpha$-Anomeric nucleic acid molecules form in particular double-stranded hybrids with complementary RNA in which the strands run parallel to one another, in contrast to the normal $\beta$ units (Gaultier et al. (1987) Nucleic Acids Res 15:6625-6641).

The use of the sequences described above in sense orientation is likewise encompassed and may, as is familiar to the skilled worker, lead to cosuppression. The expression of sense RNA to an endogenous gene may reduce or switch off its expression, similar to that described for antisense approaches (Goring et al. (1991) Proc Natl Acad Sci USA 88:1770-1774; Smith et al. (1990) Mol Gen Genet 224:447-481; Napoli et al. (1990) Plant Cell 2:279-289; Van der Krol et al. (1990) Plant Cell 2:291-299). It is moreover for the introduced construct to represent the gene to be reduced wholly or only in part. The possibility of translation is unnecessary.

It is also very particularly preferred to use processes such as gene regulation by means of double-stranded RNA (double-stranded RNA interference). Corresponding processes are known to the skilled worker and described in detail (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). Express reference is made to the processes and methods described in the indicated references. Highly efficient suppression of native genes is brought about here through simultaneous introduction of strand and complementary strand.

It is possible and advantageous to couple the antisense strategy with a ribozyme process. Ribozymes are catalytically active RNA sequences which, coupled to the antisense sequences, catalytically cleave the target sequences (Tanner N K. FEMS Microbiol Rev. 1999; 23 (3):257-75). This may increase the efficiency of an antisense strategy. Expression of ribozymes for reducing particular proteins is known to the skilled worker and described for example in EP-A1 0 291 533, EP-A1 0 321 201 and EP-A1 0 360 257. Suitable target sequences and ribozymes can be determined as described by Steinecke (Ribozymes, Methods in Cell Biology 50, Galbraith et al. eds. Academic Press, Inc. (1995), 449-460) by secondary structure calculations of ribozyme RNA and target RNA and by the interaction thereof (Bayley C C et al., Plant Mol Biol. 1992; 18(2):353-361; Lloyd A M and Davis R W et al., Mol Gen Genet. 1994 March; 242(6):653-657). Examples which should be mentioned are hammerhead ribozymes (Haselhoff and Gerlach (1988) Nature 334:585-591). Preferred ribozymes are based on derivatives of the tetrahymena L-19 IVS RNA (U.S. Pat. No. 4,987,071; U.S. Pat. No. 5,116,742). Further ribozymes having selectivity for an L119 mRNA can be selected (Bartel D and Szostak J W (1993) Science 261: 1411-1418).

In a further embodiment, target protein expression can be reduced by using nucleic acid sequences which are complementary to regulatory elements of the target protein genes, form with the latter a triple helical structure and thus prevent gene transcription (Helene C (1991) Anticancer Drug Des. 6(6):569-84; Helene C et al. (1992) Ann NY Acad Sci 660: 27-36; Maher L J (1992) Bioassays 14(12):807-815).

The bidirectional promoters of the invention are particularly advantageous when it is employed for regulating two enzymes of a metabolic pathway. 2'-Methyl-6-phytylhydroquinone methyltransferase and homogentisate phytyl-pyrophosphate-transferase, for example, can be expressed simultaneously via one of the bidirectional promoters of the invention, bringing about an increase in tocopherols. In addition, inhibition of homogentisate dioxygenase (for example by expression of a corresponding dsRNA) and overexpression of tyrosine aminotransferase leads to an increase in the tocopherol content. In carotenoid metabolism, inhibition of $\alpha$-cyclase and overexpression of $\beta$-cyclase leads to a change in the content of $\alpha$-carotene and $\beta$-carotene.

It is possible to prevent post-transcriptional silencing effects by parallel inhibition of the transcription of the SDE3 gene and overexpression of the recombinant protein (WO 02/063039).

Immunologically active parts of antibodies can also be advantageously expressed by using the promoters of the invention. Thus, for example, the heavy chain of an IgG1 antibody can be expressed in one direction, and the light chain in the other direction. The two form a functional antibody after translation (WO 02/101006).

A further possibility is to express simultaneously stress-related ion transporters (WO 03/057899) together with herbicide genes in order to increase the tolerance of environmental effects.

Many enzymes consist of two or more subunits, both of which are necessary for functioning. It is possible by means of one of the bidirectional promoters of the invention to express two subunits simultaneously. One example thereof is overexpression of the α and β subunits of follicle stimulating human hormone.

A construct consisting of a gene for a selection marker and a reporter gene is particularly valuable for establishing transformation systems, when they are regulated by this bidirectional promoter.

The expression cassettes of the invention and the vectors derived therefrom may comprise further functional elements. The term functional element is to be understood broadly and means all elements which have an influence on production, multiplication or function of the expression cassettes of the invention or vectors or organisms derived therefrom. Non-restrictive examples which may be mentioned are:

a) Reporter genes

Reporter genes or proteins code for easily quantifiable proteins and ensure via an intrinsic color or enzymic activity an assessment of transformation efficiency or of the site or time of expression (Schenborn E, Groskreutz D (1999) Mol Biotechnol 13(1):2944). Examples which should be mentioned are:

green fluorescence protein (GFP) (Chui W L et al., Curr Biol 1996, 6:325-330; Leffel S M et al., Biotechniques. 23(5):912-8, 1997; Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).

chloramphenicol transferase (Fromm et al. (1985) Proc Natl Acad Sci USA 82:5824-5828), luciferase (Millar et al. (1992) Plant Mol Biol Rep 10:324-414; Ow et al. (1986) Science, 234:856-859); permits detection of bioluminescence.

β-galactosidase, codes for an enzyme for which various chromogenic substrates are available.

β-glucuronidase (GUS) (Jefferson et al. (1987) EMBO J 6:3901-3907) or the uidA gene which encodes an enzyme for various chromogenic substrates.

R-locus gene product protein which regulates the production of anthocyanin pigments (red coloration) in plant tissues and thus makes direct analysis possible of the promoter activity without adding additional auxiliaries or chromogenic substrates (Dellaporta et al., In: Chromosome Structure and Function: Impact of New Concepts, 18th Stadler Genetics Symposium 11:263-282, 1988).

β-lactamase (Sutcliffe (1978) Proc Natl Acad Sci USA 75:3737-3741), enzyme for various chromogenic substrates (e.g. PADAC, a chromogenic cephalosporin).

xylE gene product (Zukowsky et al. (1983) Proc Natl Acad Sci USA 80:1101-1105), catechol dioxygenase, which can convert chromogenic catechols.

alpha-amylase (Ikuta et al. (1990) Bio/Technol. 8:241-242).

tyrosinase (Katz et al. (1983) J Gen Microbiol 129:2703-2714), enzyme which oxidizes tyrosine to DOPA and dopaquinone which subsequently form the easily detectable melanin.

aequorin (Prasher et al. (1985) Biochem Biophys Res Commun 126(3):1259-1268), can be used in calcium-sensitive bioluminescence detection.

b) Origins of replication which ensure a multiplication of the expression cassettes or vectors of the invention in, for example, E. coli. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

c) Elements for example "border sequences" which make agrobacteria-mediated transfer into plant cells possible for transfer and integration into the plant genome, such as, for example, the right or left border of the T-DNA or the vir region.

d) Multiple cloning regions (MCS) permit and facilitate the insertion of one or more nucleic acid sequences.

The skilled worker is aware of various ways of obtaining an expression cassette of the invention. The production of an expression cassette of the invention takes place for example by fusing one of the promoters of the invention (or a functional equivalent or functionally equivalent part as shown in SEQ ID NO: 1 or 2 or a functional equivalent with a nucleic acid sequence to be expressed, if appropriate with a sequence coding for a transit peptide, preferably a chloroplast-specific transit peptide which is preferably disposed between the promoter and the respective nucleic acid sequence, and with a terminator or polyadenylation signal. Conventional techniques of recombination and cloning are used for this purpose (as described above).

However, and expression cassette also means constructions in which the promoter, without previously having been functionally linked to a nucleic acid sequence to be expressed, is introduced into a host genome, for example via a targeted homologous recombination or a random insertion, there assumes regulatory control of nucleic acid sequences which are then functionally linked to it, and controls transgenic expression thereof. Insertion of the promoter—for example by homologous recombination—in front of a nucleic acid coding for a particular polypeptide results in an expression cassette of the invention which controls the expression of the particular polypeptide in the plant. The insertion of the promoter may also take place by expression of antisense RNA to the nucleic acid coding for a particular polypeptide. Expression of the particular polypeptide in plants is thus downregulated or switched off.

It is also possible analogously for a nucleic acid sequence to be expressed transgenically to be placed, for example by homologous recombination, behind the endogenous, natural promoter, resulting in an expression cassette of the invention which controls the expression of the nucleic acid sequence to be expressed transgenically.

Vectors comprising the expression cassettes described above are also according to the invention. Vectors may be for example plasmids, cosmids, phages, viruses or else agrobacteria.

Another aspect of the invention relates to transgenic organisms transformed with at least one expression cassette of the invention or one vector of the invention, and cells, cell cultures, tissues, parts—such as, for example, leaves, roots etc. of plant organisms—or propagation material derived from such organisms.

Organism, initial or host organisms mean prokaryotic or eukaryotic organisms such as, for example, microorganisms or plant organisms. Preferred microorganisms are bacteria, yeasts, algae or fungi.

Preferred bacteria are bacteria of the genus *Escherichia, Erwinia, Agrobacterium, Flavobacterium, Alcaligenes* or cyanobacteria for example of the genus *Synechocystis*. Particularly preferred microorganisms are those able to infect plants and thus to transfer the cassettes of the invention. Preferred microorganisms are those from the genus *Agrobacterium* and in particular of the species *Agrobacterium tumefaciens*.

Preferred yeasts are *Candida, Saccharomyces, Hansenula* or *Pichia*. Preferred fungi are *Aspergillus, Trichoderma, Ashbya, Neurospora, Fusarium, Beauveria* or further fungi described in Indian Chem Engr. Section B. Vol 37, No. 1, 2 (1995) on page 15, table 6.

Host or initial organisms preferred as transgenic organisms are in particular plants. Included for the purposes of the invention are all genera and species of higher and lower plants of the plant kingdom. Also included are mature plants, seeds, shoots and seedlings, and parts derived therefrom, propagation material and cultures, for example cell cultures. Mature plants means plants at any stage of development beyond the seedling. Seedling means a young, immature plant in an early stage of development.

Annual, perennial, monocotyledodonous and dicotyledonous plants are preferred host organisms for producing transgenic plants. Plants of the following plant families are preferred: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanacea, Sterculiaceae, Tetragoniacea, Theaceae, Umbelliferae.

Preferred monocotyledodonous plants are in particular cited from the monocotyledodonous crop plants such as, for example, of the Gramineae family, such as rice, corn, wheat or other cereal species such as barley, millet, rye, triticale or oats, and sugarcane and all grass species.

Preferred dicotyledonous plants are in particular selected from the dicotyledonous crop plants such as, for example, Asteraceae such as sunflower, tagetes or *calendula* and many others, Compositae, especially of the genus *Lactuca*, very especially of the species *sativa* (lettuce) and many others, Cruciferae, especially the genus *Brassica*, very especially the species *napus* (oilseed rape), *campestris* (beet), *oleracea* cv Tastie (cabbage), *oleracea* cv Snowball Y (cauliflower) and *oleracea* cv Emperor (broccoli) and other *brassica* species; and of the genus *Arabidopsis*, very especially the species *thaliana* and many others, Cucurbitaceae such as melon, pumpkin or zucchini and many others, Leguminosae, especially the genus *Glycine*, very especially the species max (soybean), soybean and alfalfa, pea, beans or peanut and many others Rubiaceae, preferably of the subclass Lamiidae such as, for example, *Coffea arabica* or *Coffea liberica* (coffee bush) and many others, Solanaceae, especially the genus *Lycopersicon*, very especially the species *esculentum* (tomato) and the genus *Solanum*, very especially the species *tuberosum* (potato) and *melongena* (aubergine), and tobacco or paprika and many others, Sterculiaceae, preferably of the subclass Dilleniidae such as, for example, *Theobroma cacao* (cocoa plant) and many others, Theaceae, preferably of the subclass Dilleniidae such as, for example, *Camellia sinensis* or *Thea sinensis* (tea bush) and many others, Umbelliferae, especially the genus *Daucus* (very especially the species *carota* (carrot) and *Apium* (very especially the species *graveolens dulce* (celeriac) and many others; and the genus *Capsicum*, very especially the species *annum* (pepper) and many others, and flax, soybean, cotton, hemp (flax), cucumber, spinach, carrot, sugarbeet and the various tree, nut and vine species, especially banana and kiwi fruit.

Preference is given to *Nicotiana tabacum, Tagetes erecta* und *Calendula officinalis*, and all genera and species used as human or animal foods, such as the described cereals species, or are suitable for the production of oils, such as oilseeds (such as rape), nut species, soybean, sunflower, pumpkin and peanut.

Most preference is given to all plants of the Brassicaceae family, very especially the *Brassica* species such as *Brassica napus* (oilseed rape), *campestris* (beet), *oleracea* cv Tastie (cabbage), *oleracea* cv Snowball Y (cauliflower) and *oleracea* cv Emperor (broccoli) and further *brassica* species; and of the genus *Arabidopsis*, very especially the species *thaliana*.

Plant organisms for the purposes of the invention are additionally further photosynthetically active capable organisms such as, for example, algae or cyano bacteria, and mosses. Preferred algae are green algae such as, for example, algae of the genus *Haematococcus, Phaedactylum tricomatum, Volvox* or *Dunaliella*. Particular preference is given to algae such as Chlorophyceae, Phaeophpyceae, Rhodophyceae, Myxophyceae, Xanthophyceae, Bacillariophyceae (diatoms) and Euglenophyceae.

Production of a transformed organism or of a transformed cell requires introduction of the appropriate DNA into the appropriate host cell. A large number of methods is available for this process, which is referred to as transformation (see also Keown et al. (1990) Methods in Enzymology 185:527-537). Thus, for example, the DNA can be introduced directly by microinjection or by bombardment with DNA-coated microparticles. The cell can also be permeabilized chemically, for example with polyethylene glycol, so that the DNA can enter the cell by diffusion. The DNA can also take place by protoplast fusion with other DNA-containing units such as minicells, cells, lysosomes or liposomes. Electroporation is a further method suitable for introducing DNA, in which the cells are reversibly permeabilized by an electric pulse.

In the case of plants, the described methods for transformation and regeneration of plants from plant tissues or plant cells are used for transient or stable transformation. Suitable methods are in particular protoplast transformation by polyethylene glycol-induced DNA uptake, the biolistic process using a gene gun, the so-called particle bombardment method, electroporation, incubation of dry embryos in DNA-containing solution and microinjection.

Besides these "direct" transformation techniques, it is also possible to carry out a transformation by bacterial infection with *Agrobacterium tumefaciens* or *Agrobacterium rhizogenes*. These strains comprise a plasmid (Ti or Ri plasmid) which is transferred to the plant after *agrobacterium* infection. Part of this plasmid, called T-DNA (transferred DNA), is integrated into the genome of the plant cell.

*Agrobacterium*-mediated transformation is most suitable for dicotyledonous, diploid plant cells, whereas direct transformation techniques are suitable for every cell type.

Introduction of an expression cassette of the invention into cells, preferably into plant cells, can advantageously be achieved by use of vectors.

In an advantageous embodiment, the introduction of the expression cassette is achieved by means of plasmid vectors. Preferred vectors are those making stable integration of the expression cassette into the host genome possible.

In the case of injection or electroporation of DNA into plant cells, no special requirements must be met by the plasmid used. Simple plasmid such as those of the pUC series can be used. If complete plants are to be regenerated from the transformed cells, it is necessary for an additional selectable marker gene to be present on the plasmid.

Transformation techniques are described for various monocotyledodonous and dicotyledonous plant organisms. In addition, various possible plasmid vectors are available for introducing foreign genes into plants, which ordinarily comprise an origin of replication for replication in *E. coli* and a marker gene for selection of transformed bacteria. Examples are pBR322, pUC series, M13 mp series, pACYC184 etc.

The expression cassette can be introduced into the vector via a suitable restriction cleavage site. The resulting plasmid is first introduced into *E. coli*. Correctly transformed *E. coli* are selected and cultured, and the recombinant plasmid is isolated by methods familiar to the skilled worker. Restriction analysis and sequencing can be used to check the cloning step.

Transformed cells, i.e. those which comprise the introduced DNA integrated into the DNA of the host cell, can be selected from untransformed ones if a selectable marker is a constituent of the introduced DNA. Any gene that is able to confer a resistance to antibiotics or herbicides can act for example as marker. Transformed cells expressing such as marker gene are able to survive in the presence of concentrations of an appropriate antibiotic or herbicide which kill an untransformed wild type. An example are the bar gene that confers resistance to the herbicide phosphinothricin (Rathore K S et al., Plant Mol Biol. 1993 March; 21(5):871-884), the nptII gene that confers resistance to kanamycin, the hpt gene which confers resistance to hygromycin, or the EPSP gene which confers resistance to the herbicide glyphosate.

Depending on the method for DNA introduction, further genes may be necessary on the vector plasmid. If *agrobacteria* are used, the expression cassette is to be integrated into special plasmids, either into an intermediate vector (or shuttle vector) or a binary vector. If, for example, a Ti or Ri plasmid is to be used at least the right border, but in most cases the right and the left border of the Ti or Ri plasmid T-DNA is connected as flanking region to the expression cassette to be introduced. Binary vectors are preferably used. Binary vectors can replicate both in *E. coli* and in *agrobacterium*. They ordinarily comprise a selection marker gene and a linker or polylinker flanked by the right and left T-DNA border sequence. They can be transformed directly into *agrobacterium* (Holsters et al. (1978) Mol. Gen. Genet. 163:181-187). The selection marker gene permits selection of transformed *agrobacteria* and is for example the nptII gene which confers resistance to kanamycin. The *agrobacterium* acting as host organism in this case should already comprise a plasmid having the vir region. This is necessary for transfer of the T-DNA to the plant cell. An *agrobacterium* transformed in this way can be used to transform plant cells.

The use of T-DNA for transformation of plant cells has been intensively investigated and described (EP 120516; Hoekema, In: The Binary Plant Vector System, Offsetdrukkerij Kanters B. V., Alblasserdam, Chapter V; Fraley et al. (1986) CRC Crit. Rev. Plant. Sci., 4:1-46 and An et al. (1985) EMBO J. 4:277-287). Various binary vectors are known and some are commercially available such as, for example, pBIN19 (Clontech Laboratories, Inc. U.S.A.).

DNA is transferred into the plant cell by coculturing the plant explants with *Agrobacterium tumefaciens* or *Agrobacterium rhizogenes*. Starting from infected plant material (e.g. parts of leaves, roots or stems, but also protoplasts or suspensions of plant cells), it is possible to regenerate whole plants by use of a suitable medium that may comprise for example antibiotics or biocides for selecting transformed cells. The resulting plants can then be screened for the presence of the introduced DNA, in this case the expression cassette of the invention. As soon as the DNA is integrated into the host genome, the corresponding genotype is usually stable and the corresponding insertion is also found in subsequent generations. The integrated expression cassette usually comprises a selection marker (see above). The selection marker permits selection of transformed from untransformed cells (McCormick et al. (1986) Plant Cell Rep 5:81-84). The resulting plants can be grown and crossed in the usual way. Two or more generations should be cultured in order to ensure that genomic integration is stable and inheritable.

Said processes are described for example in B. Jenes et al., Techniques for Gene Transfer, in: Transgenic Plants, Vol. 1, Engineering and Utilization, edited by Kung S D & Wu R, Academic Press (1993), pp. 128-143 and in Potrykus I (1991) Annu Rev Plant Physiol Plant Mol Biol 42:205-225). The construct to be expressed is preferably cloned into a vector which is suitable for transforming *Agrobakterium tumefaciens*, for example pBin19 (Bevan et al. (1984) Nucl Acids Res 12:8711f.).

As soon as a transformed plant cell has been produced, a complete plant can be obtained by using processes known to the skilled worker. This entails starting for example from callus cultures. The formation of shoot and root from these still undifferentiated cell masses can be induced in a known manner. The resulting shoots can be planted out and grown.

The effectiveness of the expression of the transgenically expressed nucleic acids can be measured for example in vitro by shoot meristem propagation using one of the selection methods described above.

Also according to the invention are cells, cell cultures, parts—such as, for example, roots, leaves etc. in the case of transgenic plant organisms—and transgenic propagation material such as seeds or fruits, derived from the transgenic organisms described above.

Genetically modified plants of the invention which can be consumed by humans and animals may also be used as human food or animal food for example directly or after processing in a manner known per se.

A further aspect of the invention relates to the use of the transgenic organisms of the invention described above and of the cells, cell cultures, parts—such as, for example, roots, leaves etc. in the case of transgenic plant organisms—and transgenic propagation material such as seeds or fruits derived therefrom for producing human or animal foods, pharmaceuticals or fine chemicals.

Preference is further given to a process for the recombinant production of pharmaceuticals or fine chemicals in host organisms, where a host organism is transformed with one of the expression cassettes or vectors described above, and this expression cassette comprises one or more structural genes which code for the desired fine chemical or catalyze the biosynthesis of the desired fine chemical, the transformed host organism is cultured, and the desired fine chemical is isolated from the culture medium. This process is widely applicable to fine chemicals such as enzymes, vitamins, amino acids, sugars, fatty acids, natural and synthetic flavorings, aromatizing substances and colorants. The production of tocopherols and tocotrienols, and of carotenoids is particularly preferred. The culturing of the transformed host organisms, and the isolation from the host organisms or from the culture medium takes place by means of processes known to the skilled worker. The production of pharmaceuticals such as, for example, antibodies or vaccines is described in Hood E E, Jilka J M (1999). Curr Opin Biotechnol 10(4):382-6; Ma J K, Vine N D (1999). Curr Top Microbiol Immunol 236:275-92.

Sequences

1. SEQ ID NO: 1  Bidirectional promoter from *Arabidopsis thaliana*. Intergene region between the putative FD gene and the putative OASTL gene up to in each case the assumed start of transcription.
2. SEQ ID NO: 2  Bidirectional promoter from *Arabidopsis thaliana* including the 5'-untranslated regions of the putative FD gene and of the putative OASTL gene up to in each case the ATG start codon. Compared with the native sequence, the present sequence comprises an additional C at position 4 compared with the native *Arabidopsis* sequence through introduction of a BamHI recognition sequence.
3. SEQ ID NO: 3  Sequence of the plasmid pUH200. The GUS gene is expressed in the direction of the FD gene, and the nptII gene in the direction of the OASTL gene.
4. SEQ ID NO: 4  Sequence of the plasmid pUH201. The GUS gene is expressed in the direction of the OASTL gene, and the nptII gene in the direction of the FD gene.
5. SEQ ID NO: 5  Oligonucleotide primer pFD3
5'-acggatccgagagacagagagacggagacaaaa-3'
6. SEQ ID NO: 6  Oligonucleotide primer pFD4
5'-gcggatccaagcttcactgcttaaattc-3'

EXAMPLES

General Methods

Figure 1:
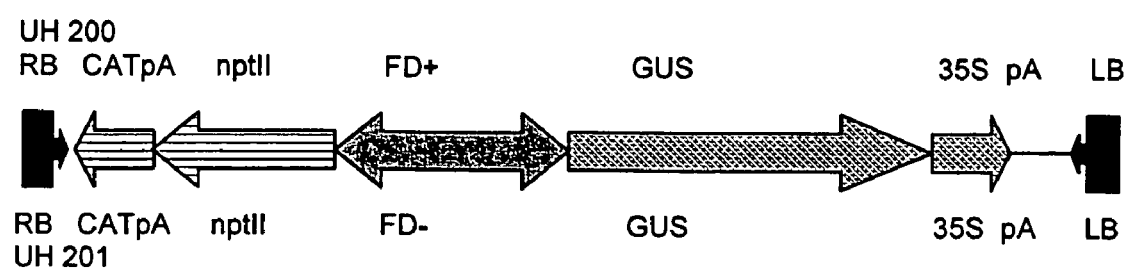
FIG. 1: Diagrammatic representation of the bidirectional unit in the vectors UH200 and UH201. RB: right border of the *agrobacterium* T-DNA; CATpA: terminator of the cathepsin D inhibitor; nptII: neomycin phosphotransferase II gene (kanamycin resistance gene); FD: intergene region between FD and OASTL gene (+/−indicate the direction of reading of the FD gene); GUS: β-glucuronidase gene; 35SpA: terminator of the 35S CaMV gene; LB: left border of the *agrobacterium* T-DNA.

Chemical synthesis of oligonucleotides can take place for example in a known manner by the phosphoamidite method (Voet, Voet, 2nd edition, Wiley Press New York, page 896-897). The cloning steps carried out for the purposes of the present invention, such as, for example, restriction cleavages, agarose gel electrophoreses, purification of DNA fragments, transfer of nucleic acids onto nitrocellulose and nylon membranes, linkage of DNA fragments, transformation of *E. coli* cells, culturing of bacteria, replication of phages and sequence analysis of recombinant DNA are carried out as described in Sambrook et al. (1989) Cold Spring Harbor Laboratory Press; ISBN 0-87969-309-6. Recombinant DNA molecules are sequenced by the method of Sanger (Sanger et al. (1977) Proc Natl Acad Sci USA 74:5463-5467) using a laser fluorescence DNA sequencer supplied by ABI.

Example 1

Isolation of DNA from *Arabidopsis thaliana*, Tobacco and Oilseed Rape

The genomic DNA from *Arabidopsis thaliana*, tobacco and oilseed rape was isolated using the DNeasy plant mini kit from Qiagen Cat. No. 60106 in accordance with the protocol.

Example 2

Transformation of Tobacco and Oilseed Rape

The transformation of tobacco took place by infection with *Agrobacterium tumefaciens* in accordance with the method developed by Horsch (Horsch et al. (1985) Science 227: 1229-1231). All the constructs used for the transformation were transformed by the freeze/thaw method (repeated thawing and freezing) into *Agrobacterium tumefaciens*. The *Agrobacterium* colonies comprising the desired construct were selected on YEB medium (1% beef extract (Difco), 0.5% casein enzyme hydrolyzate, 0.1% yeast extract (Duchefa), 0.5% sucrose, 2 mM $MgSO_4$, 1.5% agar) medium with 50 µg/ml kanamycin, 40 µg/ml gentamycin, 100 µg/ml spectinomycin and 25 µg/ml rifampicin.

Tobacco plants (*Nicotiana tabacum* L. cv. Samsun N N) were transformed by centrifuging 10 ml of an overnight culture of *Agrobacterium tumefaciens* grown under selection, discarding the supernatant, and resuspending the bacteria in the same volume of antibiotic-free medium. Leaf disks from sterile plants (diameter about 1 cm) were bathed in this bacterial solution in a sterile Petri dish. The leaf disks were then laid on MS medium (Murashige and Skoog (1962) Physiol Plant 15:473ff.) with 2% sucrose and 0.8% Bacto agar in Petri dishes. After incubation at 25° C. in the dark for 2 days, they were transferred to MS medium with 100 mg/l kanamycin, 500 mg/l Claforan, 1 mg/l benzylaminopurine (BAP), 0.2 mg/l naphtylacetic acid (NAA), 1.6% glucose and 0.8% Bacto agar, and cultivation was continued (16 hours of light/8 hours of darkness). Growing shoots were transferred to hormone-free MS medium with 2% sucrose, 250 mg/l Claforan and 0.8% Bacto agar.

Oilseed rape was transformed by means of petiole transformation by the method of Moloney et al. (Moloney M M et al. (1989) Plant Cell Rep 8:238-242).

Example 3

Investigation of Bidirectional Expression of the FD Promoter a) PCR isolation of the FD promoter from *Arabidopsis thaliana*

The putative bidirectional promoter was amplified by PCR from genomic *Arabidopsis thaliana* DNA using the primers FD3 and FD4. The nucleotides in bold print for a BamHI site were attached to the primer FD3. A BamHI site was introduced into the primer FD4 by insertion of a C (bold) as difference from the genomic sequence.

Primer FD3: (SEQ ID NO: 5)

5'-acggatccgagagacagagagacggagacaaaa-3'

Primer FD4: (SEQ ID NO: 6)

5'-gcggatccaagcttcactgcttaaattc-3'

Reaction Mixture:
  1 µl of DNA
  37 µl of $H_2O$
  5 µl of 10× buffer
  1 µl of FD3 primer 10 µM
  1 µl of FD4 primer 10 µM
  4 µl of dNTP 2.5 mM
  1 µp of Pfu turbo DNA polymerase (Stratagene)

PCR Conditions:
  1 cycle with 5 min at 95° C.
  25 cycles with 52° C. for 1 min, 72° C. for 1 min and 95° C. for 30 sec
  1 cycle with 72° C. for 10 min, subsequent cooling to 4° C. until processed further.

b) Construction of the FD:GUS Expression Cassettes

The PCR product comprising the FD promoter was cleaved with the restriction enzyme BamHI and ligated into the vector pGUSINT37 (SunGene), likewise BamHI cleaved. The undirected cloning resulted in the two plasmids pFD+GUS and pFD−GUS in which the promoter fragment is placed in front of the GUS gene in opposite orientations in each case. The plasmid pFD+GUS comprises the promoter in the direction of transcription of the putative ferredoxin gene, and the plasmid pFD−GUS in the orientation of the annotated O-acetylserine thiol-lyase gene (OASTL, cysteine synthase).

Example 4

Production of Vectors for Simultaneous Analysis of Both Directions of Transcription of the FD Promoter To analyze both directions of expression, the genes of the selection marker NptII and of the reporter glucuronidase were placed under the control of the bidirectional promoter into constructs. For this purpose, the plasmids pFD+GUS and pFD−GUS were cleaved with EcoRI/SalI and cloned into the vector pS5NptIICat (derivative of the pSUN vector; WO 02/00900). The resulting plasmids UH200 (SEQ ID NO: 3) comprises the GUS gene under the control of the transcriptional elements acting in the direction of the ferredoxin gene, and the NptII gene under the control of the transcriptional elements acting in the direction OASTL gene. In the plasmid UH201 (SEQ ID NO: 4), the GUS gene is under the control of the OASTL directed factors and the NptII gene is under the control of the elements controlling the ferredoxin gene (see FIG. 1). Both constructs were transformed into the *agrobacterium* strain GV3101[pMP90] and transformed into tobacco and oilseed rape in accordance with the protocols.

Example 5

Results of the Analysis of Kanamycin Resistance of the Transgenic Tobacco Plants Selective regeneration of tobacco plantlets took place on 100 mg/l kanamycin. 86% of the explants of the were transformed with the construct UH200 developed plumules. 89% of the cut shoots rooted on kanamycin-containing medium, and all were transgenic according to PCR analyses. 70% of the explants from the transformation experiment with UH201 developed plumules, of which 90% rooted. Once again, PCR analysis revealed that the plantlets comprised the appropriate construct and are thus transgenic. This example shows that both promoter orientations are suitable in the same way for expressing selection markers during selective regeneration of tobacco.

Example 6

Results of the Analysis of Kanamycin Resistance of the Transgenic Oilseed Rape Plants Selective regeneration of the oilseed rape shoots took place on 18 mgA kanamycin. The transformation efficiency was 11% for the construct UH200 and 10% for UH201. At the same time, the transformation efficiency under the control of the promoter of nopaline synthase was found to be 8%. This example showed that selective regeneration both under the control of the promoter in the OASTL direction (UH200) and the FD direction (UH201) is comparable with the nosP normally used.

Example 7

GUS Analysis of the Tissue Specificity of the Bidirectional Promoter in the Transgenic Tobacco and Oilseed Rape Plants The two promoter orientations have shown the same tissue specificities, with the exception in pollen, in the transgenic tobacco and oilseed rape plants (table 1). Whereas no activities were found in the pollen in oilseed rape, the tobacco pollen showed a distinct blue coloration and thus promoter activity. GUS expression regulated by both orientations was found predominantly in green tissue. No expression was detectable in roots and petals. GUS activity was detectable even in very early stages of seed development in oilseed rape.

TABLE 1

Overview of the tissue specificities in tobacco and oilseed rape.

| Tissue | | A | | B | C | D | E | F | G | H | I | J | K | L |
| --- | --- | --- | --- | --- | --- | --- | --- | --- | --- | --- | --- | --- | --- | --- |
| | | siL | soL | | | | | | | | | | | |
| Tobacco | FD | ++ | ++ | − | + | + | ++ | ++ | + | + | ++ | − | + | ++ |
| | OASTL | + | + | − | + | + | + | + | + | + | ++ | − | + | ++ |
| Rape | FD | ++ | ++ | − | ++ | nd | + | + | + | + | + | − | + | − |

++ high activity
+ lower activity
− no activity; nd: not determined
A leaves (siL: sink leaves; soL: source leaves)
B roots
C seeds
D seedling
E stem
F flower stalk
G nodes
H bud
I sepals
J petals
K anthers
L pollen.

The promoter activity during selective regeneration was followed by staining young shoots with X-Gluc. Transgenic shoots showed an intense blue stain. This experiment again showed the same activity of the bidirectional promoter in both orientations.

Example 8

Quantitative GUS Analysis of the Bidirectional Promoter in Transgenic Tobacco Plants For quantitative analysis of the strength of the FD promoter, leaf and seed material from transgenic plants of both constructs were investigated in parallel. The quantitative GUS assay was carried out in accordance with the procedure of Jefferson with MUG and 4-methylumbelliferone as standard. A similar amount of GUS activity was detected in the seeds of the plants of both orientations. Expression was distinctly measurable in leaf material in both directions, but the intensity was less uniform than in seed material.

Example 9

Figure 2:
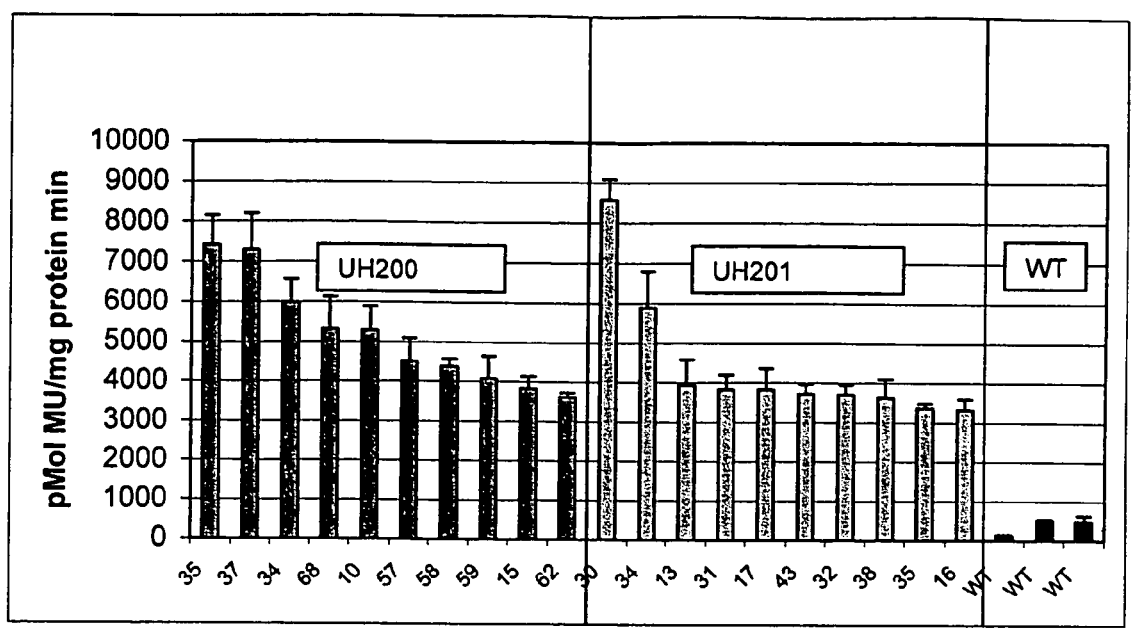
FIG. 2: Analysis of the GUS activity in leaves of transgenic oilseed rape plants transformed with UH 200 (orientation of the ferredoxin gene) or UH 201 (orientation of the OASTL gene) compared with wild type (WT) plants. The results of various lines of UH200 or UH201 transformed oilseed rape plants (identified by number of the respective line on the x axis) are shown. The GUS activity is indicated pmol methylumbelliferone (MU)/mg (protein) min.

Quantitative GUS Analysis of the Bidirectional Promoter in the Transgenic Oilseed Rape Plants Oilseed rape was transformed—as described above—likewise with the constructs UH200 and UH201. Quantitative GUS analysis of leaf material of transgenic oilseed rape plants showed that the two promoter directions showed an identical activity. FIG. 2 shows the values for the individual lines. The level of expression corresponds to the other polar plant promoters.

We claim:

1. A transgenic expression cassette for expressing two nucleic acid sequences in a plant cell comprising
   i) at least one regulatory sequence, and
   ii) at least two nucleic acid sequences which are functionally linked to and heterologous in relation to said regulatory sequence,
   wherein the regulatory sequence has bidirectional expression activity and comprises
   a) the nucleotide sequence shown in SEQ ID NO: 1 or 2, or a fragment thereof having bidirectional expression activity, or
   b) a nucleotide sequence having at least 98% identity to the nucleotide sequence shown in SEQ ID NO: 1 or 2 and having bidirectional expression activity as the nucleotide sequence shown in SEQ ID NO: 1 or 2,
   wherein said regulatory sequence is disposed between the two nucleic acid sequences in such a way that the expression of the two nucleic acid sequences is brought about in at least one plant cell, wherein said two nucleic acid sequences code for
   i) amino acid sequences, or
   ii) ribonucleic acid sequences which bring about a reduction in the expression of at least one endogenous gene of said plant cell.

2. The transgenic expression cassette according to claim 1, wherein the two nucleic acid sequences to be expressed transgenically are different and code for one of the following combinations:
   i) a selection marker and a reporter protein,
   ii) a target protein and a selection marker or a reporter protein,
   ii) two target proteins from the same metabolic pathway,
   iii) a sense RNA and an antisense RNA, or
   iv) various proteins for defense against pathogens.

3. The expression transgenic cassette according to claim 1, wherein at least one of the two nucleic acid sequences to be expressed transgenically is selected from the group consisting of nucleic acids coding for selection markers, reporter genes, cellulases, chitinases, glucanases, ribosome-inactivating proteins, lysozymes, *Bacillus thuringiensis* endotoxins, α-amylase inhibitors, protease inhibitors, lectins, RNAases, ribozymes, acetyl-CoA carboxylases, phytases, 2S albumin from Bertholletia excelsa, antifreeze proteins, trehalose-phosphate synthases, trehalose-phosphate phosphatases, trehalases, DREB1A factor, farnesyltransferases, ferritin, oxalate oxidases, calcium-dependent protein kinases, calcineurins, glutamate dehydrogenases, N-hydroxylating multifunctional cytochrome P-450, transcriptional activator CBF1, phytoene desaturases, polygalacturonases, flavonoid 3'-hydroxylases, dihydroflavanol 4-reducases, chalcone isomerases, chalcone synthases, flavanone 3-beta-hydroxylases, flavone synthase II, branching enzyme Q, and starch branching enzymes.

4. The trans genic expression cassette according to claim 1, wherein at least one of the two nucleic acid sequences to be expressed transgenically is selected from the group consisting of nucleic acids coding for positive selection markers, negative selection markers and factors which provide a growth advantage.

5. A transgenic expression vector comprising the transgenic expression cassette according to claim 1.

6. A transgenic non-human organism transformed with the transgenic expression cassette according to claim 1.

7. The transgenic non-human organism according to claim 6, wherein the transgenic non-human organism is selected from the group consisting of bacteria, yeasts, fungi, animal and plant organisms.

8. The transgenic non-human organism according to claim 6, wherein the transgenic non-human organism is selected from the group consisting of *arabidopsis*, tomato, tobacco, potatoes, corn, oilseed rape, wheat, barley, sunflowers, millet, beet, rye, oats, sugarbeet, beans and soybean.

9. A cell, cell culture, part or transgenic propagation material derived from the transgenic non-human organism according to claim 6.

10. A process for transgenic expression of two nucleic acid sequences in plant cells, comprising
   I. introducing, into plant cells, a transgenic expression cassette, wherein the transgenic expression cassette comprises at least one regulatory sequence and at least two nucleic acid sequences which are functionally linked to and heterologous in relation to said regulatory sequence, and
   II. selecting transgenic cells which comprise said expression cassette stably integrated into the genome,
   wherein the regulatory sequence has bidirectional expression activity and comprises
   a) the nucleotide sequence shown in SEQ ID NO: 1 or 2, or a fragment thereof having bidirectional expression activity, or
   b) a nucleotide sequence having at least 98% identity to the nucleotide sequence shown in SEQ ID NO: 1 or 2 and having bidirectional expression activity as the nucleotide sequence shown in SEQ ID NO: 1 or 2,
   wherein said regulatory sequence is disposed between the two nucleic acid sequences in such a way that the expression of said two nucleic acid sequences is brought about in at least said plant cell, wherein said two nucleic acid sequences code for
i) amino acid sequences, or
ii) ribonucleic acid sequences which bring about a reduction in the expression of at least one endogenous gene of said plant cell.

11. The process according to claim 10, wherein the two nucleic acid sequences to be expressed transgenically are different and code for one of the following combinations
i) a selection marker and a reporter protein,
ii) a target protein and a selection marker or a reporter protein,
ii) two target proteins from the same metabolic pathway,
iii) a sense RNA and an antisense RNA, or
iv) various proteins for defense against pathogens.

12. The transgenic expression cassette according to claim 1, wherein at least one of the two nucleic acid sequences to be expressed transgenically is a nucleic acid coding for a selection marker.

13. The transgenic expression cassette according to claim 12, wherein the selection marker is selected from the group consisting of proteins which confer a resistance to antibiotics, metabolism inhibitors, herbicides and biocides.

14. The transgenic expression cassette according to claim 12, wherein the selection marker is selected from the group consisting of proteins which confer a resistance to phosphinothricin, glyphosate, bromoxynil, dalapon, 2-deoxyglucose 6-phosphate, tetracycline, ampicillin, kanamycin, G 418, neomycin, paromomycin, bleomycin, zeocin, hygromycin, chloramphenicol, sulfonylurea herbicides, and imidazolinone herbicides.

15. The transgenic expression cassette according to claim 12, wherein the selection marker is selected from the group consisting of phosphinothricin acetyltransferases, 5-enolpyruvylshikimate-3-phosphate synthases, glyphosate oxidoreductases, dehalogenase, nitrilases, neomycin phosphotransferases, DOG$^R$1 genes, acetolactate synthases, hygromycin phosphotransferases, chloramphenicol acetyltransferases, streptomycin adenylyltransferases, β-lactamases, tetA genes, tetR genes, isopentenyltransferases, thymidine kinases, diphtheria toxin A, cytosine deaminase (codA), cytochrome P450, haloalkane dehalogenases, iaaH genes, tms2 genes, β-glucuronidases, mannose-6-phosphate isomerases, and UDP-galactose 4-epimerases.

16. The process according to claim 10, wherein at least one of the two nucleic acid sequences to be expressed transgenically is selected from the group consisting of nucleic acids coding for selection markers, reporter genes, cellulases, chitinases, glucanases, ribosome-inactivating proteins, lysozymes, *Bacillus thuringiensis* endotoxins, α-amylase inhibitors, protease inhibitors, lectins, RNAases, ribozymes, acetyl-CoA carboxylases, phytases, 2S albumin from Bertholletia excelsa, antifreeze proteins, trehalose-phosphate synthases, trehalose-phosphate phosphatases, trehalases, DREB1A factor, farnesyltransferases, ferritin, oxalate oxidases, calcium-dependent protein kinases, calcineurins, glutamate dehydrogenases, N-hydroxylating multifunctional cytochrome P-450, transcriptional activator CBF1, phytoene desaturases, polygalacturonases, flavonoid 3'-hydroxylases, dihydroflavanol 4-reducases, chalcone isomerases, chalcone synthases, flavanone 3-beta-hydroxylases, flavone synthase II, branching enzyme Q, and starch branching enzymes 17. The process according to claim 10, wherein at least one of the two nucleic acid sequences to be expressed transgenically is selected from the group consisting of nucleic acids coding for positive selection markers, negative selection markers and factors which provide a growth advantage.

18. The process according to claim 10, wherein at least one of the two nucleic acid sequences to be expressed transgenically is a nucleic acid coding for a selection marker.

19. The process according to claim 18, wherein the selection marker is selected from the group consisting of proteins which confer a resistance to antibiotics, metabolism inhibitors, herbicides and biocides.

20. The process according to claim 18, wherein the selection marker is selected from the group consisting of proteins which confer a resistance to phosphinothricin, glyphosate, bromoxynil, dalapon, 2-deoxyglucose 6-phosphate, tetracycline, ampicillin, kanamycin, G 418, neomycin, paromomycin, bleomycin, zeocin, hygromycin, chloramphenicol, sulfonylurea herbicides, and imidazolinone herbicides.

21. The process according to claim 18, wherein the selection marker is selected from the group consisting of phosphinothricin acetyltransferases, 5-enolpyruvylshikimate-3-phosphate synthases, glyphosate oxidoreductases, dehalogenase, nitrilases, neomycin phosphotransferases, DOG$^R$1 genes, acetolactate synthases, hygromycin phosphotransferases, chloramphenicol acetyltransferases, streptomycin adenylyltransferases, β-lactamases, tetA genes, tetR genes, isopentenyltransferases, thymidine kinases, diphtheria toxin A, cytosine deaminase (codA), cytochrome P450, haloalkane dehalogenases, iaaH genes, tms2 genes, β-glucuronidases, mannose-6-phosphate isomerases, and UDP-galactose 4-epimerases.

22. Human or animal foods, seeds, pharmaceuticals or fine chemicals produced from the transgenic non-human organism according to claim 6, or cell, cell cultures, parts or transgenic propagation material derived therefrom.

23. A method for identifying and/or isolating a regulatory sequence with bidirectional expression activity, comprising
preparing fragments of the nucleic acid sequence of SEQ ID NO: 1 or 2,
testing the fragments obtained for bidirectional expression, and
identifying and/or isolating a fragment with bidirectional expression activity.

24. An expression cassette for expressing two nucleic acid sequences in a plant cell comprising at least one regulatory sequence, wherein the regulatory sequence has bidirectional expression activity and comprises a fragment obtained by the method of claim 23.

25. The expression cassette of claim 24, further comprising at least two nucleic acid sequences which are functionally linked to and heterologous in relation to said regulatory sequence, wherein said regulatory sequence is disposed between the two nucleic acid sequences in such a way that the expression of the two nucleic acid sequences is brought about in at least one plant cell.

26. A method for identifying and/or isolating a regulatory sequence with bidirectional expression activity, comprising
providing the nucleic acid sequence of SEQ ID NO: 1 or 2,
obtaining variants of the nucleic acid sequence of SEQ ID NO: 1 or 2,
testing the variants obtained for bidirectional expression, and
identifying and/or isolating a variant with bidirectional expression activity.

27. An expression cassette for expressing two nucleic acid sequences in a plant cell comprising
   i) at least one regulatory sequence, and
   ii) at least two nucleic acid sequences which are functionally linked to and heterologous in relation to said regulatory sequence,
wherein the regulatory sequence has bidirectional expression activity and comprises a variant of SEQ ID NO: 1 or 2 obtained by the method of claim 26, and wherein the regulatory sequence is disposed between the two nucleic acid sequences in such a way that the expression of the two nucleic acid sequences is brought about in at least one plant cell.

28. The transgenic expression cassette of claim 1, wherein the regulatory sequence comprises the nucleotide sequence shown in SEQ ID NO: 1 or 2, or a fragment thereof having bidirectional expression activity.

* * * * *

UNITED STATES PATENT AND TRADEMARK OFFICE
CERTIFICATE OF CORRECTION

PATENT NO. : 7,557,203 B2
APPLICATION NO. : 10/565221
DATED : July 7, 2009
INVENTOR(S) : Ute Linemann et al.

Page 1 of 1

It is certified that error appears in the above-identified patent and that said Letters Patent is hereby corrected as shown below:

In the Claims:

In Claim 4, in column 54, on line 22, "4. The trans genie expression cassette according to claim 1," should read -- The transgenic expression cassette according to claim 1, --.

In Claim 16, in column 55, on line 67, "and starch branching enzymes" should read -- and starch branching enzymes. --.

Signed and Sealed this

Twenty-second Day of September, 2009

David J. Kappos
*Director of the United States Patent and Trademark Office*

SEQUENCE LISTING

```
<160> NUMBER OF SEQ ID NOS: 6

<210> SEQ ID NO 1
<211> LENGTH: 429
<212> TYPE: DNA
<213> ORGANISM: Arabidopsis thaliana
<220> FEATURE:
<221> NAME/KEY: promoter
<222> LOCATION: (1)..(429)
<223> OTHER INFORMATION: promoter

<400> SEQUENCE: 1
gtatggaata aaatcttcga atgatgagat atatgatctc tttggtgtca gtcacatggc      60
acacgctatc aatttagaaa aacgcggtgg ttggtcacca gaattactac ttctcggtct     120
gatttggtca tatccgtatt aagtccggtt aatatttcc  ataactgggg tttgaacatt     180
cggtttcttt ttttcagtta gtccgatttg gagttttgag tatggaaaaa taatactgaa     240
tttatttgtt caaactgttt tggaaaaaat atttccctta attacgaata taattaaaat     300
tttaaaattc attttattag atcttggtta attcggttta atgcattaat gaatttcggt     360
```

```
ttaagtcggt tttcggtttt tatgtcccac cactatctac aaccgatgat caaccttatc    420
tccgtattc                                                             429
```

```
<210> SEQ ID NO 2
<211> LENGTH: 836
<212> TYPE: DNA
<213> ORGANISM: Arabidopsis thaliana
<220> FEATURE:
<221> NAME/KEY: promoter
<222> LOCATION: (344)..(772)
<223> OTHER INFORMATION: promoter
<220> FEATURE:
<221> NAME/KEY: Intron
<222> LOCATION: (14)..(281)
<223> OTHER INFORMATION: 1st intron of OASTL gene
<220> FEATURE:
<221> NAME/KEY: 5'UTR
<222> LOCATION: (773)..(836)
<223> OTHER INFORMATION: 5'UTR of FD gene
<220> FEATURE:
<221> NAME/KEY: 5'UTR
<222> LOCATION: (1)..(343)
<223> OTHER INFORMATION: 5'-UTR of OASTL gene comprising intron

<400> SEQUENCE: 2
```

```
gatccaagct tcactgctta aattcacaaa aagagaaaag taagaccaaa ggaataaatc     60
atcctcaaac caaaaacaca tcatacaaaa tcatcaaaca taaatctcca gatgtatgag    120
caccaatcca gttatacaac actcttaaca ccaaatcaac agatttaaca gcgaaataag    180
cttaagccca tacaattatc cgatccaaac aaatataatc gaaaccggca gaggaataag    240
caagtgaatc aaaaagtatg ggacgaggaa gaagatgata cctgaatgag aaagtcaata    300
accttgaccc gaatcgtttt gaagaaaatg gagaaaatcg gttgtatgga ataaaatctt    360
cgaatgatga gatatatgat ctctttggtg tcagtcacat ggcacacgct atcaatttag    420
aaaaacgcgg tggttggtca ccagaattac tacttctcgg tctgatttgg tcatatccgt    480
attaagtccg gttaatattt tccataactg gggtttgaac attcggtttc ttttttttcag   540 ttagtccgat ttggagtttt gagtatgaaa aataatact gaatttattt gttcaaactg     600
ttttggaaaa aatatttccc ttaattacga atataattaa aattttaaaa ttcatttat    660 tagatcttgg ttaattcggt ttaatgcatt aatgaatttc ggtttaagtc ggttttcggt    720
ttttatgtcc caccactatc tacaaccgat gatcaacctt atctccgtat tcaccacaaa    780
cagtcatcac tctcacttga cacaaaaact cttttgtctc cgtctctctg tctctc        836
```

```
<210> SEQ ID NO 3
<211> LENGTH: 11533
<212> TYPE: DNA
<213> ORGANISM: Artificial Sequence
<220> FEATURE:
<223> OTHER INFORMATION: Expression vector UH200

<400> SEQUENCE: 3
```

```
ttccatggac atacaaatgg acgaacggat aaaccttttc acgcccttt aaatatccga     60 ttattctaat aaacgctctt ttctcttagg tttacccgcc aatatatcct gtcaaacact    120
gatagtttaa actgaaggcg ggaaacgaca atcagatcta gtaggaaaca gctatgacca    180
tgattacgcc aagcttgcat gccgatcccc ccactccgc cctacactcg tatatatatg    240
cctaaacctg ccccgttcct catatgtgat attattattt cattattagg tataagatag    300
```

-continued

| | |
|---|---|
| taaacgataa ggaaagacaa tttattgaga aagccatgct aaaatataga tagatatacc | 360 |
| ttagcaggtg tttatttac aacataacat aacatagtag ctagccagca ggcaggctaa | 420 |
| aacatagtat agtctatctg caggggtac ggtcgactct agactagtgg atccgtcgaa | 480 |
| gctagcttgg gtcccgctca aagaactcg tcaagaaggc gatagaaggc gatgcgctgc | 540 |
| gaatcgggag cggcgatacc gtaaagcacg aggaagcggt cagcccattc gccgccaagc | 600 |
| tcttcagcaa tatcacgggt agccaacgct atgtcctgat agcggtccgc cacacccagc | 660 |
| cggccacagt cgatgaatcc agaaaagcgg ccattttcca ccatgatatt cggcaagcag | 720 |
| gcatcgccat gggtcacgac gagatcctcg ccgtcgggca tgcgcgcctt gagcctggcg | 780 |
| aacagttcgg ctggcgcgag cccctgatgc tcttcgtcca gatcatcctg atcgacaaga | 840 |
| ccggcttcca tccgagtacg tgctcgctcg atgcgatgtt tcgcttggtg gtcgaatggg | 900 |
| caggtagccg gatcaagcgt atgcagccgc cgcattgcat cagccatgat ggatactttc | 960 |
| tcggcaggag caaggtgaga tgacaggaga tcctgccccg cacttcgcc caatagcagc | 1020 |
| cagtcccttc ccgcttcagt gacaacgtcg agcacagctg cgcaaggaac gcccgtcgtg | 1080 |
| gccagccacg atagccgcgc tgcctcgtcc tgcagttcat tcagggcacc ggacaggtcg | 1140 |
| gtcttgacaa aaagaaccgg gcgcccctgc gctgacagcc ggaacacggc ggcatcagag | 1200 |
| cagccgattg tctgttgtgc ccagtcatag ccgaatagcc tctccaccca gcggccgga | 1260 |
| gaacctgcgt gcaatccatc ttgttcaatc caagctccca tgggccctcg actagagtcg | 1320 |
| agatccgata tcgcccgggc tcgactctag aggatccaag cttcactgct taaattcaca | 1380 |
| aaaagagaaa agtaagacca aaggaataaa tcatcctcaa accaaaaaca catcatacaa | 1440 |
| aatcatcaaa cataaatctc cagatgtatg agcaccaatc cagttataca acactcttaa | 1500 |
| caccaaatca acagatttaa cagcgaaata agcttaagcc catacaatta tccgatccaa | 1560 |
| acaaatataa tcgaaaccgg cagaggaata agcaagtgaa tcaaaaagta tgggacgagg | 1620 |
| aagaagatga tacctgaatg agaaagtcaa taaccttgac ccgaatcgtt ttgaagaaaa | 1680 |
| tggagaaaat cggttgtatg gaataaaatc ttcgaatgat gagatatatg atctctttgg | 1740 |
| tgtcagtcac atggcacacg ctatcaattt agaaaaacgc ggtggttggt caccagaatt | 1800 |
| actacttctc ggtctgattt ggtcatatcc gtattaagtc cggttaatat tttccataac | 1860 |
| tggggtttga acattcggtt tcttttttc agttagtccg atttggagtt ttgagtatgg | 1920 |
| aaaaataata ctgaatttat ttgttcaaac tgttttggaa aaaatatttc ccttaattac | 1980 |
| gaatataatt aaaattttaa aattcatttt attagatctt ggttaattcg gtttaatgca | 2040 |
| ttaatgaatt tcggtttaag tcggttttcg gttttatgt cccaccacta tctacaaccg | 2100 |
| atgatcaacc ttatctccgt attcaccaca aacagtcatc actctcactt gacacaaaaa | 2160 |
| ctcttttgtc tccgtctctc tgtctctcgg atccccgggt aggtcagtcc cttatgttac | 2220 |
| gtcctgtaga aaccccaacc cgtgaaatca aaaaactcga cggcctgtgg gcattcagtc | 2280 |
| tggatcgcga aaactgtgga attggtcagc gttggtggga agcgcgtta caagaaagcc | 2340 |
| gggcaattgc tgtgccagga gtttttaacg atcaagttcg ccgatgccag atattcgtaa | 2400 |
| ttatgccggc aacgtcttgg tatcagcgcc gaagtcttta ttccgaaagg ttgggcaggc | 2460 |
| cagcgtatcg tgctgcgttt cgatgcggtc actcattacg gcaaagtgtg gtcaataat | 2520 |
| caggaagtga tggagcatca gggcggctat acgccatttg aagccgatgt cacgccgtat | 2580 |
| gttattgccg ggaaaagtgt acgtaagttt ctgcttctac ctttgatata tatataataa | 2640 |

```
ttatcattaa ttagtagtaa tataatattt caaatatttt tttcaaaata aaagaatgta    2700
gtatatagca attgcttttc tgtagtttat aagtgtgtat attttaattt ataacttttc    2760
taatatatga ccaaaatttg ttgatgtgca ggtatcaccg tttgtgtgaa caacgaactg    2820
aactggcaga ctatcccgcc gggaatggtg attaccgacg aaaacggcaa gaaaaagcag    2880
tcttacttcc atgatttctt taactatgcc ggaatccatc gcagcgtaat gctctacacc    2940
acgccgaaca cctgggtgga cgatatcacc gtggtgacgc atgtcgcgca agactgtaac    3000
cacgcgtctg ttgactggca ggtggtggcc aatggtgatg tcagcgttga actgcgtgat    3060
gcggatcaac aggtggttgc aactggacaa ggcactagcg ggactttgca agtggtgaat    3120
ccgcacctct ggcaaccggg tgaaggttat ctctatgaac tgtgcgtcac agccaaaagc    3180
cagacagagt gtgatatcta cccgcttcgc gtcggcatcc ggtcagtggc agtgaagggc    3240
gaacagttcc tgattaacca caaaccgttc tactttactg gctttggtcg tcatgaagat    3300
gcggacttac gtggcaaagg attcgataac gtgctgatgg tgcacgacca cgcattaatg    3360
gactggattg ggccaactc ctaccgtacc tcgcattacc cttacgctga agagatgctc    3420
gactgggcag atgaacatgg catcgtggtg attgatgaaa ctgctgctgt cggctttaac    3480
ctctctttag gcattggttt cgaagcgggc aacaagccga agaactgta cagcgaagag    3540 gcagtcaacg gggaaactca gcaagcgcac ttacaggcga ttaaagagct gatagcgcgt    3600
gacaaaaacc acccaagcgt ggtgatgtgg agtattgcca acgaaccgga tacccgtccg    3660
caagtgcacg gaatatttc gccactggcg gaagcaacgc gtaaactcga cccgacgcgt    3720
ccgatcacct gcgtcaatgt aatgttctgc gacgctcaca ccgataccat cagcgatctc    3780
tttgatgtgc tgtgcctgaa ccgttattac ggatggtatg tccaaagcgg cgatttggaa    3840
acggcagaga aggtactgga aaaagaactt ctggcctggc aggagaaact gcatcagccg    3900
attatcatca ccgaatacgg cgtggatacg ttagccgggc tgcactcaat gtacaccgac    3960
atgtggagtg aagagtatca gtgtgcatgg ctggatatgt atcaccgcgt ctttgatcgc    4020
gtcagcgccg tcgtcggtga acaggtatgg aatttcgccg attttgcgac ctcgcaaggc    4080
atattgcgcg ttggcggtaa caagaaaggg atcttcactc gcgaccgcaa accgaagtcg    4140
gcggcttttc tgctgcaaaa acgctggact ggcatgaact tcggtgaaaa accgcagcag    4200
ggaggcaaac aatgaatcaa caactctcct ggcgcaccat cgtcggctac agcctcggga    4260
attgctaccg agctcggtac ccggcgcaaa aatcaccagt ctctctctac aaatctatct    4320
ctctctattt ttctccagaa taatgtgtga gtagttccca gataagggaa ttagggttct    4380
tatagggttt cgctcatgtg ttgagcatat aagaaaccct tagtatgtat ttgtatttgt    4440
aaaatacttc tatcaataaa atttctaatt cctaaaacca aaatccagtg accgggtacc    4500
gagctcgaat tcactggccg tcgttttaca acgactcagc agcttgacag gaggcccgat    4560
ctagtaacat agatgacacc gcgcgcgata atttatccta gtttgcgcgc tatattttgt    4620
tttctatcgc gtattaaatg tataattgcg ggactctaat cataaaaacc catctcataa    4680
ataacgtcat gcattacatg ttaattatta catgcttaac gtaattcaac agaaattata    4740
tgataatcat cgcaagaccg gcaacaggat tcaatcttaa gaaactttat tgccaaatgt    4800
ttgaacgatc ggggatcatc cgggtctgtg gcgggaactc cacgaaaata tccgaacgca    4860
gcaagatcgg tcgatcgact cagatctggg taactggcct aactggcctt ggaggagctg    4920
gcaactcaaa atccctttgc caaaaaccaa catcatgcca tccaccatgc ttgtatccag    4980
```

```
ccgcgcgcaa tgtaccccgc gctgtgtatc ccaaagcctc atgcaaccta acagatggat    5040
cgtttggaag gcctataaca gcaaccacag acttaaaacc ttgcgcctcc atagacttaa    5100
gcaaatgtgt gtacaatgta gatcctaggc ccaacctttg atgcctatgt gacacgtaaa    5160
cagtactctc aactgtccaa tcgtaagcgt tcctagcctt ccagggccca gcgtaagcaa    5220
taccagccac aacaccctca acctcagcaa ccaaccaagg gtatctatct tgcaacctct    5280
ctaggtcatc aatccactct tgtggtgttt gtggctctgt cctaaagttc actgtagacg    5340
tctcaatgta atggttaacg atgtcacaaa ccgcggccat atcggctgct gtagctggcc    5400
taatctcaac tggtctcctc tccgagaca tgtcgagatt atttggattg agagtgaata    5460
tgagactcta attggatacc gaggggaatt tatggaacgt cagtggagca ttttgacaa    5520 gaaatatttg ctagctgata gtgaccttag gcgacttttg aacgcgcaat aatggtttct    5580
gacgtatgtg cttagctcat taaactccag aaacccgcgg ctgagtggct ccttcaacgt    5640
tgcggttctg tcagttccaa acgtaaaacg gcttgtcccg cgtcatcggc gggggtcata    5700
acgtgactcc cttaattctc cgctcatgat cagattgtcg tttcccgcct tcagtttaaa    5760
ctatcagtgt ttgacaggat cctgcttggt aataattgtc attagattgt ttttatgcat    5820
agatgcactc gaaatcagcc aattttagac aagtatcaaa cggatgttaa ttcagtacat    5880
taaagacgtc cgcaatgtgt tattaagttg tctaagcgtc aatttgttta caccacaata    5940
tatcctgcca ccagccagcc aacagctccc cgaccggcag ctcggcacaa aatcaccacg    6000
cgttaccacc acgccggccg gccgcatggt gttgaccgtg ttcgccggca ttgccgagtt    6060
cgagcgttcc ctaatcatcg accgcacccg gagcgggcgc gaggccgcca aggcccgagg    6120
cgtgaagttt ggcccccgcc ctaccctcac cccggcacag atcgcgcacg cccgcgagct    6180
gatcgaccag gaaggccgca ccgtgaaaga ggcggctgca ctgcttggcg tgcatcgctc    6240
gaccctgtac cgcgcacttg agcgcagcga ggaagtgacg cccaccgagg ccaggcggcg    6300
cggtgccttc cgtgaggacg cattgaccga ggccgacgcc ctggcggccg ccgagaatga    6360
acgccaagag gaacaagcat gaaaccgcac caggacggcc aggacgaacc gttttttcatt    6420 accgaagaga tcgaggcgga gatgatcgcg gccgggtacg tgttcgagcc gccgcgcgcac    6480 gtctcaaccg tgcggctgca tgaaatcctg gccggtttgt ctgatgccaa gctggcggcc    6540
tggccggcca gcttggccgc tgaagaaacc gagcgccgcc gtctaaaaag gtgatgtgta    6600
tttgagtaaa acagcttgcg tcatgcggtc gctgcgtata tgatgcgatg agtaaataaa    6660
caaatacgca aggggaacgc atgaaggtta tcgctgtact taaccagaaa ggcgggtcag    6720
gcaagacgac catcgcaacc catctagccc gcgccctgca actcgccggg gccgatgttc    6780
tgttagtcga ttccgatccc cagggcagtg cccgcgattg gcggccgtg cgggaagatc    6840 aaccgctaac cgttgtcggc atcgaccgcc cgacgattga ccgcgacgtg aaggccatcg    6900
gccggcgcga cttcgtagtg atcgacgag cgccccaggc ggcggacttg gctgtgtccg    6960
cgatcaaggc agccgacttc gtgctgattc cggtgcagcc aagcccttac gacatatggg    7020
ccaccgccga cctggtggag ctggttaagc agcgcattga ggtcacggat ggaaggctac    7080
aagcggcctt tgtcgtgtcg cgggcgatca aaggcacgcg catcggcggt gaggttgccg    7140
aggcgctggc cgggtacgag ctgcccattc ttgagtcccg tatcacgcag cgcgtgagct    7200
acccaggcac tgccgccgcc ggcacaaccg ttcttgaatc agaacccgag ggcgacgctg    7260
cccgcgaggt ccaggcgctg gccgctgaaa ttaaatcaaa actcatttga gttaatgagg    7320
```

```
taaagagaaa atgagcaaaa gcacaaacac gctaagtgcc ggccgtccga gcgcacgcag   7380
cagcaaggct gcaacgttgg ccagcctggc agacacgcca gccatgaagc gggtcaactt   7440
tcagttgccg gcggaggatc acaccaagct gaagatgtac gcggtacgcc aaggcaagac   7500
cattaccgag ctgctatctg aatacatcgc gcagctacca gagtaaatga gcaaatgaat   7560
aaatgagtag atgaattta gcggctaaag gaggcggcat ggaaaatcaa gaacaaccag    7620
gcaccgacgc cgtggaatgc cccatgtgtg gaggaacggg cggttggcca ggcgtaagcg   7680
gctgggttgt ctgccggccc tgcaatggca ctggaaccc caagcccgag gaatcggcgt    7740
gagcggtcgc aaaccatccg gcccggtaca atcggcgcg cgctgggtg atgacctggt     7800 ggagaagttg aaggccgcgc aggccgccca gcggcaacgc atcgaggcag aagcacgccc   7860
cggtgaatcg tggcaagcgg ccgctgatcg aatccgcaaa gaatcccggc aaccgccggc   7920
agccggtgcg ccgtcgatta ggaagccgcc caagggcgac gagcaaccag attttttcgt   7980
tccgatgctc tatgacgtgg gcacccgcga tagtcgcagc atcatggacg tggccgtttt   8040
ccgtctgtcg aagcgtgacc gacgagctgg cgaggtgatc cgctacgagc ttccagacgg   8100
gcacgtagag gttccgcag ggccggccgg catggccagt gtgtgggatt acgacctggt    8160
actgatggcg gtttcccatc taaccgaatc catgaaccga taccgggaag ggaagggaga   8220
caagcccggc cgcgtgttcc gtccacacgt tgcggacgta ctcaagttct gccggcgagc   8280
cgatggcgga aagcagaaag acgacctggt agaaacctgc attcggttaa acaccacgca   8340
cgttgccatg cagcgtacga agaaggccaa gaacggccgc ctggtgacgg tatccgaggg   8400
tgaagccttg attagccgct acaagatcgt aaagagcgaa accgggcggc cggagtacat   8460
cgagatcgag ctagctgatt ggatgtaccg cgagatcaca gaaggcaaga acccggacgt   8520
gctgacggtt caccccgatt acttttgat cgatcccggc atcggccgtt ttctctaccg    8580
cctggcacgc cgcgccgcag gcaaggcaga agccagatgg ttgttcaaga cgatctacga   8640
acgcagtggc agcgccggag agttcaagaa gttctgtttc accgtgcgca agctgatcgg   8700
gtcaaatgac ctgccggagt acgatttgaa ggaggaggcg gggcaggctg ccccgatcct   8760
agtcatgcgc taccgcaacc tgatcgaggg cgaagcatcc gccggttcct aatgtacgga   8820
gcagatgcta gggcaaattg ccctagcagg ggaaaaaggt cgaaaaggtc tctttcctgt   8880
ggatagcacg tacattggga acccaaagcc gtacattggg aaccggaacc cgtacattgg   8940
gaacccaaag ccgtacattg gaaccggtc acacatgtaa gtgactgata taaaagagaa    9000 aaaggcgat ttttccgcct aaaactcttt aaaacttatt aaaactctta aaacccgcct     9060
ggcctgtgca taactgtctg ccagcgcac agccgaagag ctgcaaaaag cgcctaccct    9120
tcggtcgctg cgctccctac gccccgccgc ttcgcgtcgg cctatcgcgg ccgctggccg   9180
ctcaaaaatg gctggcctac ggccaggcaa tctaccaggg cgcggacaag ccgcgccgtc   9240
gccactcgac cgccgcgcc cacatcaagg caccctgcct cgcgcgtttc ggtgatgacg    9300
gtgaaaacct ctgacacatg cagctcccgg agacggtcac agcttgtctg taagcggatg   9360
ccgggagcag acaagcccgt cagggcgcgt cagcgggtgt tggcgggtgt cggggcgcag   9420
ccatgaccca gtcacgtagc gatagcggag tgtatactgg cttaactatg cggcatcaga   9480
gcagattgta ctgagagtgc accatatgcg gtgtgaaata ccgcacagat gcgtaaggag   9540
aaaataccgc atcaggcgct cttccgcttc ctcgctcact gactcgctgc gctcggtcgt   9600
tcggctgcgg cgagcggtat cagctcactc aaaggcggta atacggttat ccacagaatc   9660
```

```
agggggataac gcaggaaaga acatgtgagc aaaaggccag caaaaggcca ggaaccgtaa      9720
aaaggccgcg ttgctggcgt ttttccatag gctccgcccc cctgacgagc atcacaaaaa      9780
tcgacgctca agtcagaggt ggcgaaaccc gacaggacta taaagatacc aggcgtttcc      9840
ccctggaagc tccctcgtgc gctctcctgt tccgaccctg ccgcttaccg gatacctgtc      9900
cgcctttctc ccttcgggaa gcgtggcgct ttctcatagc tcacgctgta ggtatctcag      9960
ttcggtgtag gtcgttcgct ccaagctggg ctgtgtgcac gaaccccccg ttcagcccga     10020
ccgctgcgcc ttatccggta actatcgtct tgagtccaac ccggtaagac acgacttatc     10080
gccactggca gcagccactg gtaacaggat tagcagagcg aggtatgtag gcggtgctac     10140
agagttcttg aagtggtggc ctaactacgg ctacactaga aggacagtat ttggtatctg     10200
cgctctgctg aagccagtta ccttcggaaa aagagttggt agctcttgat ccggcaaaca     10260
aaccaccgct ggtagcggtg gttttttgt ttgcaagcag cagattacgc gcagaaaaaa      10320
aggatctcaa gaagatcctt tgatctttc tacgggtct gacgctcagt ggaacgaaaa      10380
ctcacgttaa gggattttgg tcatgcatga tatatctccc aatttgtgta gggcttatta     10440
tgcacgctta aaaataataa aagcagactt gacctgatag tttggctgtg agcaattatg     10500
tgcttagtgc atctaacgct tgagttaagc cgcgccgcga agcggcgtcg gcttgaacga     10560
atttctagct agacattatt tgccgactac cttggtgatc tcgcctttca cgtagtggac     10620
aaattcttcc aactgatctg cgcgcgaggc caagcgatct tcttcttgtc caagataagc     10680
ctgtctagct tcaagtatga cgggctgata ctgggccggc aggcgctcca ttgcccagtc     10740
ggcagcgaca tccttcggcg cgattttgcc ggttactgcg ctgtaccaaa tgcgggacaa     10800
cgtaagcact acatttcgct catcgccagc ccagtcgggc ggcgagttcc atagcgttaa     10860
ggtttcattt agcgcctcaa atagatcctg ttcaggaacc ggatcaaaga gttcctccgc     10920
cgctggacct accaaggcaa cgctatgttc tcttgctttt gtcagcaaga tagccagatc     10980
aatgtcgatc gtggctggct cgaagatacc tgcaagaatg tcattgcgct gccattctcc     11040
aaattgcagt tcgcgcttag ctggataacg ccacggaatg atgtcgtcgt gcacaacaat     11100
ggtgacttct acagcgcgga gaatctcgct ctctccaggg gaagccgaag tttccaaaag     11160
gtcgttgatc aaagctcgcc gcgttgtttc atcaagcctt acggtcaccg taaccagcaa     11220
atcaatatca ctgtgtggct tcaggccgcc atccactgcg gagccgtaca aatgtacggc     11280
cagcaacgtc ggttcgagat ggcgctcgat gacgccaact acctctgata gttgagtcga     11340
tacttcggcg atcaccgctt ccccccatgat gtttaacttt gttttagggc gactgccctg     11400
ctgcgtaaca tcgttgctgc tccataacat caaacatcga cccacggcgt aacgcgcttg     11460
ctgcttggat gcccgaggca tagactgtac cccaaaaaaa cagtcataac aagccatgaa     11520
aaccgccact gcg                                                        11533

<210> SEQ ID NO 4
<211> LENGTH: 11533
<212> TYPE: DNA
<213> ORGANISM: Artificial Sequence
<220> FEATURE:
<223> OTHER INFORMATION: Expression vector UH201

<400> SEQUENCE: 4
ttccatggac atacaaatgg acgaacggat aaacctttc acgcccttt aaatatccga        60 ttattctaat aaacgctctt ttctcttagg tttacccgcc aatatatcct gtcaaacact      120
```

-continued

| | |
|---|---|
| gatagtttaa actgaaggcg ggaaacgaca atcagatcta gtaggaaaca gctatgacca | 180 |
| tgattacgcc aagcttgcat gccgatcccc cccactccgc cctacactcg tatatatatg | 240 |
| cctaaacctg ccccgttcct catatgtgat attattattt cattattagg tataagatag | 300 |
| taaacgataa ggaaagacaa tttattgaga aagccatgct aaaatataga tagatatacc | 360 |
| ttagcaggtg tttattttac aacataacat aacatagtag ctagccagca ggcaggctaa | 420 |
| aacatagtat agtctatctg caggggggtac ggtcgactct agactagtgg atccgtcgaa | 480 |
| gctagcttgg gtcccgctca gaagaactcg tcaagaaggc gatagaaggc gatgcgctgc | 540 |
| gaatcgggag cggcgatacc gtaaagcacg aggaagcggt cagcccattc gccgccaagc | 600 |
| tcttcagcaa tatcacgggt agccaacgct atgtcctgat agcggtccgc cacacccagc | 660 |
| cggccacagt cgatgaatcc agaaaagcgg ccatttccca ccatgatatt cggcaagcag | 720 |
| gcatcgccat gggtcacgac gagatcctcg ccgtcgggca tgcgcgcctt gagcctggcg | 780 |
| aacagttcgg ctggcgcgag ccctgatgc tcttcgtcca gatcatcctg atcgacaaga | 840 |
| ccggcttcca tccgagtacg tgctcgctcg atgcgatgtt tcgcttggtg gtcgaatggg | 900 |
| caggtagccg gatcaagcgt atgcagccgc cgcattgcat cagccatgat ggatactttc | 960 |
| tcggcaggag caaggtgaga tgacaggaga tcctgccccg gcacttcgcc caatagcagc | 1020 |
| cagtcccttc ccgcttcagt gacaacgtcg agcacagctg cgcaaggaac gcccgtcgtg | 1080 |
| gccagccacg atagccgcgc tgcctcgtcc tgcagttcat tcagggcacc ggacaggtcg | 1140 |
| gtcttgacaa aaagaaccgg gcgcccctgc gctgacagcc ggaacacggc ggcatcagag | 1200 |
| cagccgattg tctgttgtgc ccagtcatag ccgaatagcc tctccaccca agcggccgga | 1260 |
| gaacctgcgt gcaatccatc ttgttcaatc caagctccca tgggccctcg actagagtcg | 1320 |
| agatccgata tcgcccgggc tcgactctag aggatccaag cttcactgct taaattcaca | 1380 |
| aaaagagaaa agtaagacca aaggaataaa tcatcctcaa accaaaaaca catcatacaa | 1440 |
| aatcatcaaa cataaatctc cagatgtatg agcaccaatc cagttataca acactcttaa | 1500 |
| caccaaaatca acagatttaa cagcgaaata agcttaagcc catacaatta tccgatccaa | 1560 |
| acaaatataa tcgaaaccgg cagaggaata agcaagtgaa tcaaaaagta tgggacgagg | 1620 |
| aagaagatga tacctgaatg agaaagtcaa taaccttgac ccgaatcgtt ttgaagaaaa | 1680 |
| tggagaaaat cggttgtatg gaataaaatc ttcgaatgat gagatatatg atctctttgg | 1740 |
| tgtcagtcac atggcacacg ctatcaattt agaaaaacgc ggtggttggt caccagaatt | 1800 |
| actacttctc ggtctgattt ggtcatatcc gtattaagtc cggttaatat tttccataac | 1860 |
| tgggggtttga acattcggtt tctttttttc agttagtccg atttggagtt ttgagtatgg | 1920 |
| aaaaataata ctgaatttat ttgttcaaac tgttttggaa aaaatatttc ccttaattac | 1980 |
| gaatataatt aaaattttaa aattcatttt attagatctt ggttaattcg gtttaatgca | 2040 |
| ttaatgaatt tcggtttaag tcggttttcg gtttttatgt cccaccacta tctacaaccg | 2100 |
| atgatcaacc ttatctccgt attcaccaca aacagtcatc actctcactt gacacaaaaa | 2160 |
| ctcttttgtc tccgtctctc tgtctctcgg atccccgggt aggtcagtcc cttatgttac | 2220 |
| gtcctgtaga aaccccaacc cgtgaaatca aaaaactcga cggcctgtgg gcattcagtc | 2280 |
| tggatcgcga aaactgtgga attggtcagc gttggtggga aagcgcgtta caagaaagcc | 2340 |
| gggcaattgc tgtgccagga gttttttaacg atcaagttcg ccgatgccag atattcgtaa | 2400 |
| ttatgccggc aacgtcttgg tatcagcgcc gaagtcttta ttccgaaagg ttgggcaggc | 2460 |

```
cagcgtatcg tgctgcgttt cgatgcggtc actcattacg gcaaagtgtg ggtcaataat    2520
caggaagtga tggagcatca gggcggctat acgccatttg aagccgatgt cacgccgtat    2580
gttattgccg ggaaaagtgt acgtaagttt ctgcttctac ctttgatata tatataataa    2640
ttatcattaa ttagtagtaa tataatattt caaatatttt tttcaaaata aaagaatgta    2700
gtatatagca attgcttttc tgtagtttat aagtgtgtat attttaattt ataacttttc    2760
taatatatga ccaaaatttg ttgatgtgca ggtatcaccg tttgtgtgaa caacgaactg    2820
aactggcaga ctatcccgcc gggaatggtg attaccgacg aaaacggcaa gaaaaagcag    2880
tcttacttcc atgatttctt taactatgcc ggaatccatc gcagcgtaat gctctacacc    2940
acgccgaaca cctgggtgga cgatatcacc gtggtgacgc atgtcgcgca agactgtaac    3000
cacgcgtctg ttgactggca ggtggtggcc aatggtgatg tcagcgttga actgcgtgat    3060
gcggatcaac aggtggttgc aactggacaa ggcactagcg ggactttgca agtggtgaat    3120
ccgcacctct ggcaaccggg tgaaggttat ctctatgaac tgtgcgtcac agccaaaagc    3180
cagacagagt gtgatatcta cccgcttcgc gtcggcatcc ggtcagtggc agtgaagggc    3240
gaacagttcc tgattaacca caaaccgttc tactttactg gctttggtcg tcatgaagat    3300
gcggacttac gtggcaaagg attcgataac gtgctgatgg tgcacgacca cgcattaatg    3360
gactggattg gggccaactc ctaccgtacc tcgcattacc cttacgctga agagatgctc    3420
gactgggcag atgaacatgg catcgtggtg attgatgaaa ctgctgctgt cggctttaac    3480
ctctctttag gcattggttt cgaagcgggc aacaagccga agaactgta cagcgaagag    3540 gcagtcaacg gggaaactca gcaagcgcac ttacaggcga ttaaagagct gatagcgcgt    3600
gacaaaaacc acccaagcgt ggtgatgtgg agtattgcca acgaaccgga tacccgtccg    3660
caagtgcacg ggaatatttc gccactggcg gaagcaacgc gtaaactcga cccgacgcgt    3720
ccgatcacct gcgtcaatgt aatgttctgc gacgctcaca ccgataccat cagcgatctc    3780
tttgatgtgc tgtgcctgaa ccgttattac ggatggtatg tccaaagcgg cgatttggaa    3840
acggcagaga aggtactgga aaaagaactt ctggcctggc aggagaaact gcatcagccg    3900
attatcatca ccgaatacgg cgtggatacg ttagccgggc tgcactcaat gtacaccgac    3960
atgtggagtg aagagtatca gtgtgcatgg ctggatatgt atcaccgcgt ctttgatcgc    4020
gtcagcgccg tcgtcggtga acaggtatgg aatttcgccg attttgcgac ctcgcaaggc    4080
atattgcgcg ttggcggtaa caagaaaggg atcttcactc gcgaccgcaa accgaagtcg    4140
gcggcttttc tgctgcaaaa acgctggact ggcatgaact tcggtgaaaa accgcagcag    4200
ggaggcaaac aatgaatcaa caactctcct ggcgcaccat cgtcggctac agcctcggga    4260
attgctaccg agctcggtac ccggcgcaaa aatcaccagt ctctctctac aaatctatct    4320
ctctctattt ttctccagaa taatgtgtga gtagttccca gataagggaa ttagggttct    4380
tatagggttt cgctcatgtg ttgagcatat aagaaaccct tagtatgtat ttgtatttgt    4440
aaaatacttc tatcaataaa atttctaatt cctaaaacca aaatccagtg accgggtacc    4500
gagctcgaat tcactggccg tcgttttaca acgactcagc agcttgacag gaggcccgat    4560
ctagtaacat agatgacacc gcgcgcgata atttatccta gtttgcgcgc tatattttgt    4620
tttctatcgc gtattaaatg tataattgcg ggactctaat cataaaaacc catctcataa    4680
ataacgtcat gcattacatg ttaattatta catgcttaac gtaattcaac agaaattata    4740
tgataatcat cgcaagaccg gcaacaggat tcaatcttaa gaaactttat tgccaaatgt    4800
```

-continued

```
ttgaacgatc gggatcatc cgggtctgtg gcgggaactc cacgaaaata tccgaacgca      4860
gcaagatcgg tcgatcgact cagatctggg taactggcct aactggcctt ggaggagctg      4920
gcaactcaaa atcccctttgc caaaaaccaa catcatgcca tccaccatgc ttgtatccag     4980
ccgcgcgcaa tgtaccccgc gctgtgtatc ccaaagcctc atgcaaccta acagatggat     5040
cgtttggaag gcctataaca gcaaccacag acttaaaacc ttgcgcctcc atagacttaa      5100
gcaaatgtgt gtacaatgta gatcctaggc ccaacctttg atgcctatgt gacacgtaaa     5160
cagtactctc aactgtccaa tcgtaagcgt tcctagcctt ccagggccca gcgtaagcaa     5220
taccagccac aacaccctca acctcagcaa ccaaccaagg gtatctatct tgcaacctct     5280
ctaggtcatc aatccactct tgtggtgttt gtggctctgt cctaaagttc actgtagacg     5340
tctcaatgta atggttaacg atgtcacaaa ccgcggccat atcggctgct gtagctggcc     5400
taatctcaac tggtctcctc tccggagaca tgtcgagatt atttggattg agagtgaata     5460
tgagactcta attggatacc gaggggaatt tatggaacgt cagtggagca tttttgacaa     5520
gaaatatttg ctagctgata gtgaccttag gcgacttttg aacgcgcaat aatggtttct     5580
gacgtatgtg cttagctcat taaactccag aaacccgcgg ctgagtggct ccttcaacgt     5640
tgcggttctg tcagttccaa acgtaaaacg gcttgtcccg cgtcatcggc ggggtcata      5700 acgtgactcc cttaattctc cgctcatgat cagattgtcg tttcccgcct tcagtttaaa     5760
ctatcagtgt ttgacaggat cctgcttggt aataattgtc attagattgt ttttatgcat     5820
agatgcactc gaaatcagcc aattttagac aagtatcaaa cggatgttaa ttcagtacat     5880
taaagacgtc cgcaatgtgt tattaagttg tctaagcgtc aatttgttta caccacaata     5940
tatcctgcca ccagccagcc aacagctccc cgaccggcag ctcggcacaa atcaccacg      6000 cgttaccacc acgccggccg gccgcatggt gttgaccgtg ttcgccggca ttgccgagtt     6060
cgagcgttcc ctaatcatcg accgcacccg gagcgggcgc gaggccgcca aggcccgagg     6120
cgtgaagttt ggcccccgcc ctaccctcac cccggcacag atcgcgcacg cccgcgagct     6180
gatcgaccag gaaggccgca ccgtgaaaga ggcggctgca ctgcttggcg tgcatcgctc     6240
gaccctgtac cgcgcacttg agcgcagcga ggaagtgacg cccaccgagg ccaggcggcg     6300
cggtgccttc cgtgaggacg cattgaccga ggccgacgcc ctgcggccg ccgagaatga      6360 acgccaagag gaacaagcat gaaaccgcac caggacggcc aggacgaacc gttttttcatt   6420 accgaagaga tcgaggcgga gatgatcgcg gccgggtacg tgttcgagcc gcccgcgcac     6480
gtctcaaccg tgcggctgca tgaaatcctg gccggtttgt ctgatgccaa gctggcggcc     6540
tggccggcca gcttggccgc tgaagaaacc gagcgccgcc gtctaaaaag gtgatgtgta     6600
tttgagtaaa acagcttgcg tcatgcggtc gctgcgtata tgatgcgatg agtaaataaa     6660
caaatacgca aggggaacgc atgaaggtta tcgctgtact taaccagaaa ggcgggtcag     6720
gcaagacgac catcgcaacc catctagccc gcgccctgca actcgccggg gccgatgttc     6780
tgttagtcga ttccgatccc cagggcagtg cccgcgattg ggcggccgtg cgggaagatc     6840
aaccgctaac cgttgtcggc atcgaccgcc cgacgattga ccgcgacgtg aaggccatcg     6900
gccggcgcga cttcgtagtg atcgacgag cgccccaggc ggcggacttg gctgtgtccg      6960
cgatcaaggc agccgacttc gtgctgattc cggtgcagcc aagcccttac gacatatggg     7020
ccaccgccga cctggtggag ctggttaagc agcgcattga ggtcacggat ggaaggctac     7080
aagcggcctt tgtcgtgtcg cgggcgatca aaggcacgcg catcggcggt gaggttgccg     7140
```

```
aggcgctggc cgggtacgag ctgcccattc ttgagtcccg tatcacgcag cgcgtgagct   7200
acccaggcac tgccgccgcc ggcacaaccg ttcttgaatc agaacccgag ggcgacgctg   7260
cccgcgaggt ccaggcgctg ccgctgaaa ttaaatcaaa actcatttga gttaatgagg    7320
taaagagaaa atgagcaaaa gcacaaacac gctaagtgcc ggccgtccga gcgcacgcag   7380
cagcaaggct gcaacgttgg ccagcctggc agacacgcca gccatgaagc gggtcaactt   7440
tcagttgccg gcggaggatc acaccaagct gaagatgtac gcggtacgcc aaggcaagac   7500
cattaccgag ctgctatctg aatacatcgc gcagctacca gagtaaatga gcaaatgaat   7560
aaatgagtag atgaatttta gcggctaaag gaggcggcat ggaaaatcaa gaacaaccag   7620
gcaccgacgc cgtggaatgc ccatgtgtg gaggaacggg cggttggcca ggcgtaagcg    7680
gctgggttgt ctgccggccc tgcaatggca ctggaacccc caagcccgag gaatcggcgt   7740
gagcggtcgc aaaccatccg gcccggtaca atcggcgcg cgctgggtg atgacctggt     7800 ggagaagttg aaggccgcgc aggccgccca gcggcaacgc atcgaggcag aagcacgccc   7860
cggtgaatcg tggcaagcgg ccgctgatcg aatccgcaaa gaatcccggc aaccgccggc   7920
agccggtgcg ccgtcgatta ggaagccgcc caagggcgac gagcaaccag atttttcgt    7980 tccgatgctc tatgacgtgg gcacccgcga tagtcgcagc atcatggacg tggccgtttt   8040
ccgtctgtcg aagcgtgacc gacgagctgg cgaggtgatc cgctacgagc ttccagacgg   8100
gcacgtagag gtttccgcag ggccggccgg catggccagt gtgtgggatt cgacctggt    8160 actgatggcg gtttcccatc taccgaatc catgaaccga taccgggaag ggaagggaga    8220
caagcccggc cgcgtgttcc gtccacacgt tgcggacgta ctcaagttct gccggcgagc   8280
cgatggcgga aagcagaaag acgacctggt agaaacctgc attcggttaa acaccacgca   8340
cgttgccatg cagcgtacga agaaggccaa gaacggccgc ctggtgacgg tatccgaggg   8400
tgaagccttg attagccgct acaagatcgt aaagagcgaa accgggcggc ggagtacat    8460 cgagatcgag ctagctgatt ggatgtaccg cgagatcaca gaaggcaaga acccggacgt   8520
gctgacggtt caccccgatt acttttgat cgatcccggc atcggccgtt ttctctaccg    8580
cctggcacgc cgcgccgcag gcaaggcaga agccagatgg ttgttcaaga cgatctacga   8640
acgcagtggc agcgccggag agttcaagaa gttctgtttc accgtgcgca agctgatcgg   8700
gtcaaatgac ctgccggagt acgatttgaa ggaggaggcg gggcaggctg ccccgatcct   8760
agtcatgcgc taccgcaacc tgatcgaggg cgaagcatcc gccggttcct aatgtacgga   8820
gcagatgcta gggcaaattg ccctagcagg ggaaaaaggt cgaaaaggtc tctttcctgt    8880
ggatagcacg tacattggga acccaaagcc gtacattggg aaccggaacc cgtacattgg   8940
gaacccaaag ccgtacattg gaaccggtc acacatgtaa gtgactgata taaaagagaa     9000
aaaaggcgat ttttccgcct aaaactcttt aaaacttatt aaaactctta aaacccgcct    9060
ggcctgtgca taactgtctg gccagcgcac agccgaagag ctgcaaaaag cgcctaccct   9120
tcggtcgctg cgctccctac gccccgccgc ttcgcgtcgg cctatcgcgg ccgctggccg   9180
ctcaaaaatg gctggcctac ggccaggcaa tctaccaggg cgcggacaag ccgcgccgtc   9240
gccactcgac cgccggcgcc cacatcaagg caccctgcct cgcgcgtttc ggtgatgacg   9300
gtgaaaacct ctgacacatg cagctcccgg agacggtcac agcttgtctg taagcggatg   9360
ccgggagcag acaagcccgt cagggcgcgt cagcgggtgt tggcgggtgt cggggcgcag   9420
ccatgaccca gtcacgtagc gatagcggag tgtatactgg cttaactatg cggcatcaga   9480
```

```
gcagattgta ctgagagtgc accatatgcg gtgtgaaata ccgcacagat gcgtaaggag   9540
aaaataccgc atcaggcgct cttccgcttc ctcgctcact gactcgctgc gctcggtcgt   9600
tcggctgcgg cgagcggtat cagctcactc aaaggcggta atacggttat ccacagaatc   9660 agggggataac gcaggaaaga acatgtgagc aaaaggccag caaaaggcca ggaaccgtaa   9720
aaaggccgcg ttgctggcgt ttttccatag gctccgcccc cctgacgagc atcacaaaaa   9780
tcgacgctca agtcagaggt ggcgaaaccc gacaggacta taaagatacc aggcgtttcc   9840
ccctggaagc tccctcgtgc gctctcctgt tccgaccctg ccgcttaccg gatacctgtc   9900
cgcctttctc ccttcgggaa gcgtggcgct ttctcatagc tcacgctgta ggtatctcag   9960
ttcggtgtag tcgttcgct ccaagctggg ctgtgtgcac gaaccccccg ttcagcccga  10020
ccgctgcgcc ttatccggta actatcgtct tgagtccaac ccggtaagac acgacttatc  10080
gccactggca gcagccactg gtaacaggat tagcagagcg aggtatgtag gcggtgctac  10140
agagttcttg aagtggtggc ctaactacgg ctacactaga aggacagtat ttggtatctg  10200
cgctctgctg aagccagtta ccttcggaaa aagagttggt agctcttgat ccggcaaaca  10260
aaccaccgct ggtagcggtg gtttttttgt ttgcaagcag cagattacgc gcagaaaaaa  10320
aggatctcaa gaagatcctt tgatcttttc tacggggtct gacgctcagt ggaacgaaaa  10380
ctcacgttaa gggattttgg tcatgcatga tatatctccc aatttgtgta gggcttatta  10440
tgcacgctta aaaataataa aagcagactt gacctgatag tttggctgtg agcaattatg  10500
tgcttagtgc atctaacgct tgagttaagc cgcgccgcga agcggcgtcg gcttgaacga  10560
atttctagct agacattatt tgccgactac cttggtgatc tcgcctttca cgtagtggac  10620
aaattcttcc aactgatctg cgcgcgaggc caagcgatct tcttcttgtc caagataagc  10680
ctgtctagct tcaagtatga cgggctgata ctgggccggc aggcgctcca ttgcccagtc  10740
ggcagcgaca tccttcggcg cgattttgcc ggttactgcg ctgtaccaaa tgcgggacaa  10800
cgtaagcact acatttcgct catcgccagc ccagtcgggc ggcgagttcc atagcgttaa  10860
ggtttcattt agcgcctcaa atagatcctg ttcaggaacc ggatcaaaga gttcctccgc  10920
cgctggacct accaaggcaa cgctatgttc tcttgctttt gtcagcaaga tagccagatc  10980
aatgtcgatc gtggctggct cgaagatacc tgcaagaatg tcattgcgct gccattctcc  11040
aaattgcagt tcgcgcttag ctggataacg ccacggaatg atgtcgtcgt gcacaacaat  11100
ggtgacttct acagcgcgga gaatctcgct ctctccaggg gaagccgaag tttccaaaag  11160
gtcgttgatc aaagctcgcc gcgttgtttc atcaagcctt acggtcaccg taaccagcaa  11220
atcaatatca ctgtgtggct tcaggccgcc atccactgcg gagccgtaca aatgtacggc  11280
cagcaacgtc ggttcgagat ggcgctcgat gacgccaact acctctgata gttgagtcga  11340
tacttcggcg atcaccgctt ccccccatgat gtttaacttt gttttagggc gactgccctg  11400
ctgcgtaaca tcgttgctgc tccataacat caaacatcga cccacggcgt aacgcgcttg  11460
ctgcttggat gcccgaggca tagactgtac cccaaaaaaa cagtcataac aagccatgaa  11520
aaccgccact gcg                                                    11533

<210> SEQ ID NO 5
<211> LENGTH: 33
<212> TYPE: DNA
<213> ORGANISM: Artificial Sequence
<220> FEATURE:
<223> OTHER INFORMATION: Oligonucleotide primer
```

```
-continued

<400> SEQUENCE: 5
acggatccga gagacagaga gacggagaca aaa                                    33

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 6
gcggatccaa gcttcactgc ttaaattc                                          28
```